US010577398B2

(12) United States Patent
Sodoyer et al.

(10) Patent No.: US 10,577,398 B2
(45) Date of Patent: *Mar. 3, 2020

(54) MULTIMERIZATION OF RECOMBINANT PROTEIN BY FUSION TO A SEQUENCE FROM LAMPREY

(71) Applicant: Sanofi Pasteur, Lyons (FR)

(72) Inventors: Régis Sodoyer, Saint Genis les Ollières (FR); Isabelle Legastelois, Saint Andéol le Château (FR)

(73) Assignee: Sanofi Pasteur, Lyons (FR)

( * ) Notice: Subject to any disclaimer, the term of this patent is extended or adjusted under 35 U.S.C. 154(b) by 0 days.

This patent is subject to a terminal disclaimer.

(21) Appl. No.: 16/143,079

(22) Filed: Sep. 26, 2018

(65) Prior Publication Data

US 2019/0016760 A1 Jan. 17, 2019

Related U.S. Application Data

(63) Continuation of application No. 15/536,726, filed as application No. PCT/EP2015/080653 on Dec. 18, 2015, now Pat. No. 10,118,951.

(30) Foreign Application Priority Data

Dec. 19, 2014 (EP) .................................... 14307096

(51) Int. Cl.

| | |
|---|---|
| ***C07K 14/705*** | (2006.01) |
| ***A61K 39/00*** | (2006.01) |
| ***C07K 14/00*** | (2006.01) |
| ***C07K 14/46*** | (2006.01) |
| ***C07K 14/725*** | (2006.01) |
| ***C07K 14/005*** | (2006.01) |
| ***C12N 15/62*** | (2006.01) |
| *C07K 19/00* | (2006.01) |

(52) U.S. Cl.

CPC .......... *C07K 14/005* (2013.01); *C07K 14/461* (2013.01); *C12N 15/62* (2013.01); *C07K 19/00* (2013.01); *C07K 2319/00* (2013.01); *C07K 2319/21* (2013.01); *C12N 2760/16122* (2013.01); *C12N 2760/16134* (2013.01); *C12N 2800/22* (2013.01)

(58) Field of Classification Search

CPC ................ C07K 14/7051; C07K 19/00; C07K 2319/00; C07K 14/461; A61K 2035/124

See application file for complete search history.

(56) References Cited

U.S. PATENT DOCUMENTS

2012/0213780 A1 8/2012 Zhu et al.

FOREIGN PATENT DOCUMENTS

| | | | |
|---|---|---|---|
| JP | 2009545322 | A | 12/2009 |
| WO | 2008016854 | A2 | 2/2008 |
| WO | 2009090493 | A2 | 7/2009 |
| WO | 2011073692 | A1 | 6/2011 |
| WO | 2012128580 | A1 | 9/2012 |
| WO | 2014127231 | A1 | 8/2014 |

OTHER PUBLICATIONS

International Search Report issued in PCT/EP2015/080653 dated Mar. 17, 2016.

Lee, S.C. et al., "Design of a binding scaffold based on variable lymphocyte receptors of jawless vertebrates by module engineering", PNAS, 109(9):3299-3304 (2012).

Ammann, J.U. et al., "Detection of weak receptor-ligand interactions using IgM and J-chain-based fusion proteins" Eur. J. Immunol., (2012), vol. 42, pp. 1354-1356.

Barrett, B.S. et al., "Formulation and Immunogenicity Studies of Type III Secretion System Needle Antigens as Vaccine Candidates" J. Pharm. Sci., (2010), vol. 99, No. 11, pp. 4488-4496.

Czajkowsky, D.M. et al., "Fc-fusion proteins: new developments and future perspectives" EMBO Mol. Med., (2012), vol. 4, pp. 1015-1028.

Feshchenko, E. et al., "Pandemic influenza vaccine: characterization of A/California/07/2009 (H1N1) recombinant hemagglutinin protein and insights into H1N1 antigen stability" BMC Biotechnology, (2012), vol. 12, Article No. 77 (pp. 1-13).

Hashiguchi, et al., "Beyond antibody using phage display:molecular targeting by novel designed molecule" Seikagaku: The Journal of Japanese Biochemical Society, (2010), vol. 82, No. 8, pp. 710-726.

Herrin, B.R. and Cooper, M.D., "Alternative Adaptive Immunity in Jawless Vertebrates" J. Immunol., (2010), vol. 185, pp. 1367-1374.

Herrin, B.R. et al., "B Cells and Antibodies and Jawless Vertebrates" Molecular Biology of B Cells, (Nov. 3, 2014), 2nd Edition, pp. 121-132.

Herrin, B.R. et al., "Structure and specificity of lamprey monoclonal antibodies" Proc. Natl. Acad. Sci. USA, (2008), vol. 105, No. 6, pp. 2040-2045.

Li, J. et al., "Analysis of the assembly mechanism for multimeric lamprey VLRB antibodies (43.19)" J. Immunol. (Online), (May 5, 2016), vol. 184, No. 1, Suppl., p. 43.19, [Retrieved on Nov. 7, 2019], Retrieved from the Internet, URL, https://www.jimmunol.org/content/184/1_Supplement/43.19 Print Ver. [Li, J. et al., J. Immunol., (2010), vol. 184, No. 1, Suppl., p. 43.19].

(Continued)

*Primary Examiner* — Barry A Chestnut

(74) *Attorney, Agent, or Firm* — McNeill Baur PLLC

(57) ABSTRACT

The present invention relates to polymerized recombinant proteins, to recombinant nucleic acids coding for the polymerized recombinant proteins, to expression cassettes comprising the recombinant nucleic acids, to host cells transformed by the expression cassettes and to a method for multimerizing a recombinant protein. The polymerized proteins of the invention may be used in pharmaceutical or immunogenic compositions. In particular, the recombinant proteins may be antigens, antibodies or scaffolds. In particular, the polymerized recombinant protein may be an influenza haemagglutinin.

20 Claims, 9 Drawing Sheets

Specification includes a Sequence Listing.

(56) References Cited

OTHER PUBLICATIONS

Markham, A.P. et al., "Formulation and immunogenicity of a potential multivalent type III secretion system-based protein vaccine" J. Pharm. Sci., (2010), vol. 99, No. 11, pp. 4497-4509.

Mekhaiel, D.N.A. et al.,"Polymeric human Fc-fusion proteins with modified effector functions" Sci. Rep., (2011), vol. 1, Article No. 124 (pp. 1-11).

Official Action Summary issued in JP 2017-529712 dated Nov. 19, 2019.

Olafsen, T. et al., "IgM secretory tailpiece drives multimerisation of bivalent scFv fragments in eukaryotic cells" Immunotechnology, (1998), vol. 4, pp. 141-153.

Smith, R.I.F. et al. "Addition of a μ-tailpiece to IgG results in polymeric antibodies with enhanced effector functions including complement-mediated cytolysis by IgG4" J. Immunol., (1995), vol. 154, pp. 2226-2236.

Sorensen, V. et al., "Effect of the IgM and IgA secretory tailpieces on polymerization and secretion of IgM and IgG" J. Immunol., (1996), vol. 156, pp. 2858-2865.

Tasumi, S. et al., "High-affinity lamprey VLRA and VLRB monoclonal antibodies" Proc Natl. Acad. Sci. USA, (2009), vol. 106, No. 31, pp. 12891-12896.

Wright, G.J., "Signal initiation in biological systems: the properties and detection of transient extracellular protein interactions" Mol. BioSyst., (2009), vol. 5, pp. 1405-1412.

Yu, C. et al., "Purification and identification of cell surface antigens using lamprey monoclonal antibodies" J. Immunol. Methods, (2012), vol. 386, pp. 43-49.

(a)

(b)

(c)

(d)

Shuffle

Figure 9
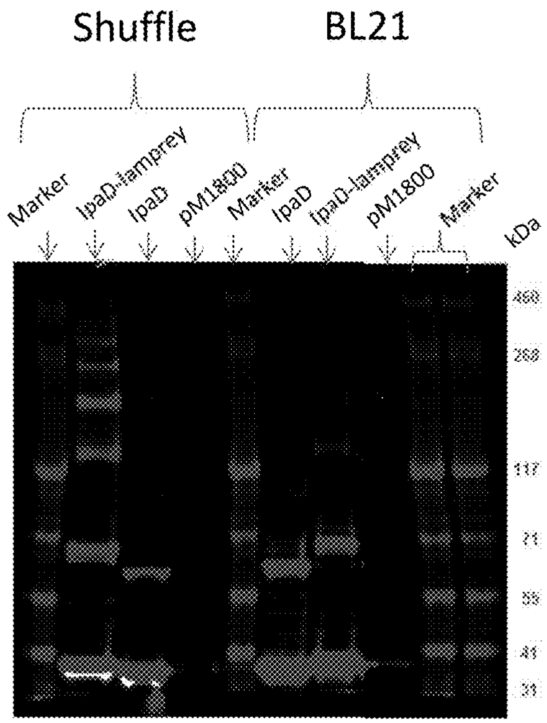
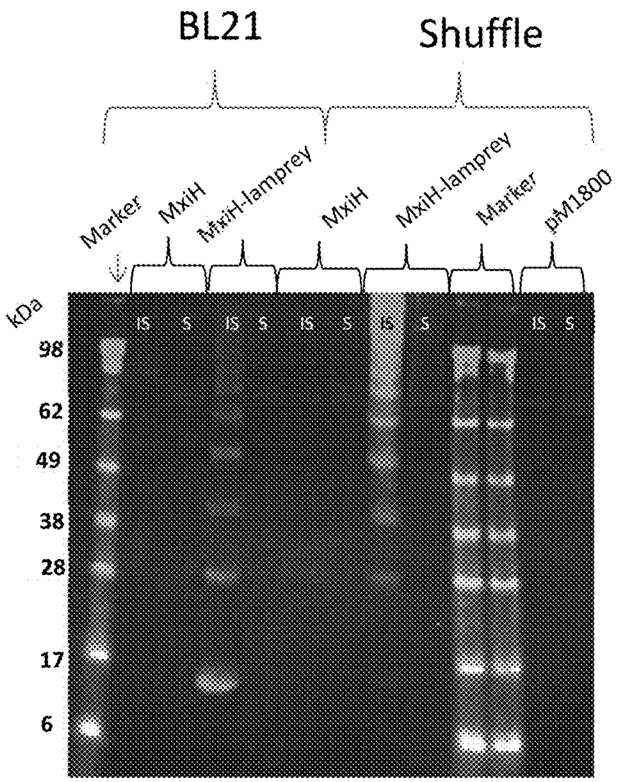
Figure 10

SEQUENCE LISTING

<160> NUMBER OF SEQ ID NOS: 29

<210> SEQ ID NO 1
<211> LENGTH: 30
<212> TYPE: PRT
<213> ORGANISM: Unknown
<220> FEATURE:
<223> OTHER INFORMATION: Petromyzontidae

<400> SEQUENCE: 1

```
Asp Cys Gly Lys Pro Ala Cys Thr Thr Leu Leu Asn Cys Ala Asn Phe
1               5                   10                  15

Leu Ser Cys Leu Cys Ser Thr Cys Ala Leu Cys Arg Lys Arg
            20                  25                  30
```

<210> SEQ ID NO 2
<211> LENGTH: 43
<212> TYPE: PRT
<213> ORGANISM: Unknown
<220> FEATURE:
<223> OTHER INFORMATION: Petromyzontidae

<400> SEQUENCE: 2

```
Asn Cys Thr Ser Ile Gln Glu Arg Lys Asn Asp Gly Gly Asp Cys Gly
1               5                   10                  15

Lys Pro Ala Cys Thr Thr Leu Leu Asn Cys Ala Asn Phe Leu Ser Cys
            20                  25                  30

Leu Cys Ser Thr Cys Ala Leu Cys Arg Lys Arg
        35                  40
```

<210> SEQ ID NO 3
<211> LENGTH: 90
<212> TYPE: DNA
<213> ORGANISM: Unknown
<220> FEATURE:
<223> OTHER INFORMATION: Petromyzontidae
<220> FEATURE:
<221> NAME/KEY: source
<222> LOCATION: (1)..(90)
<223> OTHER INFORMATION: /mol_type="unassigned DNA" /organism=
"Petromyzontidae"

<400> SEQUENCE: 3

```
gattgcggca aaccggcgtg caccaccctg ctgaactgcg cgaactttct gagctgcctg     60

tgcagcacct gcgcgctgtg ccgcaaacgc                                      90
```

<210> SEQ ID NO 4
<211> LENGTH: 129
<212> TYPE: DNA
<213> ORGANISM: Unknown
<220> FEATURE:
<223> OTHER INFORMATION: Petromyzontidae
<220> FEATURE:
<221> NAME/KEY: source
<222> LOCATION: (1)..(129)
<223> OTHER INFORMATION: /mol_type="unassigned DNA" /organism=
"Petromyzontidae"

<400> SEQUENCE: 4

```
aactgcacca gcattcagga acgcaaaaac gatggcggcg attgcggcaa accggcgtgc     60

accaccctgc tgaactgcgc gaactttctg agctgcctgt gcagcacctg cgcgctgtgc    120

cgcaaacgc                                                            129
```

<210> SEQ ID NO 5

-continued

<211> LENGTH: 29
<212> TYPE: PRT
<213> ORGANISM: Unknown
<220> FEATURE:
<223> OTHER INFORMATION: T4-like viruses

<400> SEQUENCE: 5

Gly Ser Gly Tyr Ile Pro Glu Ala Pro Arg Asp Gly Gln Ala Tyr Val
1 5 10 15

Arg Lys Asp Gly Glu Trp Val Leu Leu Ser Thr Phe Leu
20 25

<210> SEQ ID NO 6
<211> LENGTH: 87
<212> TYPE: DNA
<213> ORGANISM: Unknown
<220> FEATURE:
<223> OTHER INFORMATION: T4-like viruses
<220> FEATURE:
<221> NAME/KEY: source
<222> LOCATION: (1)..(87)
<223> OTHER INFORMATION: /mol_type="unassigned DNA" /organism="T4-like viruses"

<400> SEQUENCE: 6
ggcagcggct atattccgga agcgccgcgc gatggccagg cgtatgtgcg caaagatggc 60
gaatgggtgc tgctgagcac ctttctg 87

<210> SEQ ID NO 7
<211> LENGTH: 1680
<212> TYPE: DNA
<213> ORGANISM: Artificial Sequence
<220> FEATURE:
<223> OTHER INFORMATION: Influenza virus HA fused to lamprey multimerizing shortened sequence
<220> FEATURE:
<221> NAME/KEY: source
<222> LOCATION: (1)..(1680)
<223> OTHER INFORMATION: /mol_type="unassigned DNA" /note="Influenza virus HA fused to lamprey multimerizing shortened sequence" /organism="Artificial Sequence"

<400> SEQUENCE: 7
atgaaggcga tcctggtggt gctgctgtac acgttcgcga cggccaacgc ggatacgctg 60
tgcatcggct accacgcgaa caacagcacg gacaccgtgg acacggtgct cgagaagaac 120
gtgacggtga cgcacagcgt gaacctgctt gaggacaagc acaacggcaa gctgtgcaag 180
ctgcgtggcg tggctccgct gcacctgggc aagtgcaaca ttgctggctg gatcctgggc 240
aacccagagt gcgagagcct gagcacggcg tcgtcttgga gctacatcgt ggagacgccg 300
agcagcgaca acggcacgtg ctatccgggt gacttcatcg actacgaaga gctgcgcgag 360
cagctgtcgt cggtgagcag ctttgaacgc ttcgagattt tccccaagac gagcagctgg 420
ccgaaccacg actcgaacaa gggcgtgacg gctgcgtgtc cacacgctgg tgccaagagc 480
ttctacaaga acctgatctg gctggtgaag aagggcaaca gctacccgaa gctgagcaag 540
agctacatca acgacaaggg caaagaagtg ctcgtcctgt ggggcatcca ccacccgagc 600
acgagcgctg accagcagag cctgtaccag aacgccgaca cctacgtgtt cgtgggcagc 660
agccgctaca gcaagaagtt caagcccgag atcgcgattc gtccaaaggt gcgcgaccaa 720
gagggtcgca tgaactacta ctggacgctc gtggagccag gcgacaagat cacgttcgag 780
gcgacgggca acctggtcgt gccacgctac gccttcgcca tggaacgcaa cgctggcagc 840
ggcatcatca tcagcgacac gccagtgcac gactgcaaca cgacgtgcca gacgccgaag 900

-continued ggtgcgatca acacgagcct gccgttccag aacatccacc cgatcacgat cggcaagtgc 960
ccgaagtacg tgaagagcac gaagctgcgc ctggcgacgg gtctgcgcaa catcccgagc 1020
atccagtctc gtggtctgtt tggcgctatc gctggcttca tcgagggtgg ctggacgggc 1080
atggtggacg gctggtacgg ctaccaccac cagaacgagc agggcagcgg ctacgctgcg 1140
gacctgaagt cgacgcagaa cgcgatcgac gagatcacga acaaggtgaa cagcgtgatc 1200
gagaagatga acacgcagtt cacggctgtg ggcaaagagt tcaaccacct tgagaagcgc 1260
atcgagaacc tgaacaagaa ggtggacgac ggcttcctgg acatctggac gtacaacgcg 1320
gagctgctgg tgctgcttga gaacgagcgc acgctggact accacgattc gaacgtgaag 1380
aacctctacg agaaggtgcg cagccagctg aagaacaacg cgaaagagat cggcaacggc 1440
tgcttcgagt tctaccacaa gtgcgacaac acgtgcatgg aaagcgtgaa gaacggcacg 1500
tacgactacc cgaagtactc ggaagaggcc aagctgaacc gcgaagagat cgacggcgtg 1560
aagcttgaga gcacgcgcat ctaccaggat tgcggcaaac cggcgtgcac caccctgctg 1620
aactgcgcga actttctgag ctgcctgtgc agcacctgcg cgctgtgccg caaacgctag 1680

<210> SEQ ID NO 8
<211> LENGTH: 1719
<212> TYPE: DNA
<213> ORGANISM: Artificial Sequence
<220> FEATURE:
<223> OTHER INFORMATION: Influenza virus HA ectodomain fused to lamprey multimering sequence
<220> FEATURE:
<221> NAME/KEY: source
<222> LOCATION: (1)..(1719)
<223> OTHER INFORMATION: /mol_type="unassigned DNA" /note="Influenza virus HA ectodomain fused to lamprey multimering sequence" /organism="Artificial Sequence"

<400> SEQUENCE: 8
atgaaggcga tcctggtggt gctgctgtac acgttcgcga cggccaacgc ggatacgctg 60
tgcatcggct accacgcgaa caacagcacg gacaccgtgg acacggtgct cgagaagaac 120
gtgacggtga cgcacagcgt gaacctgctt gaggacaagc acaacggcaa gctgtgcaag 180
ctgcgtggcg tggctccgct gcacctgggc aagtgcaaca ttgctggctg gatcctgggc 240
aacccagagt gcgagagcct gagcacggcg tcgtcttgga gctacatcgt ggagacgccg 300
agcagcgaca acggcacgtg ctatccgggt gacttcatcg actacgaaga gctgcgcgag 360
cagctgtcgt cggtgagcag ctttgaacgc ttcgagattt tccccaagac gagcagctgg 420
ccgaaccacg actcgaacaa gggcgtgacg gctgcgtgtc cacacgctgg tgccaagagc 480
ttctacaaga acctgatctg gctggtgaag aagggcaaca gctacccgaa gctgagcaag 540
agctacatca acgacaaggg caaagaagtg ctcgtcctgt ggggcatcca ccacccgagc 600
acgagcgctg accagcagag cctgtaccag aacgccgaca cctacgtgtt cgtgggcagc 660
agccgctaca gcaagaagtt caagcccgag atcgcgattc gtccaaaggt gcgcgaccaa 720
gagggtcgca tgaactacta ctggacgctc gtggagccag gcgacaagat cacgttcgag 780
gcgacgggca acctggtcgt gccacgctac gccttcgcca tggaacgcaa cgctggcagc 840
ggcatcatca tcagcgacac gccagtgcac gactgcaaca cgacgtgcca gacgccgaag 900
ggtgcgatca acacgagcct gccgttccag aacatccacc cgatcacgat cggcaagtgc 960
ccgaagtacg tgaagagcac gaagctgcgc ctggcgacgg gtctgcgcaa catcccgagc 1020
atccagtctc gtggtctgtt tggcgctatc gctggcttca tcgagggtgg ctggacgggc 1080

-continued atggtggacg gctggtacgg ctaccaccac cagaacgagc agggcagcgg ctacgctgcg 1140
gacctgaagt cgacgcagaa cgcgatcgac gagatcacga acaaggtgaa cagcgtgatc 1200
gagaagatga acacgcagtt cacggctgtg ggcaaagagt tcaaccacct tgagaagcgc 1260
atcgagaacc tgaacaagaa ggtggacgac ggcttcctgg acatctggac gtacaacgcg 1320
gagctgctgg tgctgcttga gaacgagcgc acgctggact accacgattc gaacgtgaag 1380
aacctctacg agaaggtgcg cagccagctg aagaacaacg cgaaagagat cggcaacggc 1440
tgcttcgagt tctaccacaa gtgcgacaac acgtgcatgg aaagcgtgaa gaacggcacg 1500
tacgactacc cgaagtactc ggaagaggcc aagctgaacc gcgaagagat cgacggcgtg 1560
aagcttgaga gcacgcgcat ctaccagaac tgcaccagca ttcaggaacg caaaaacgat 1620
ggcggcgatt gcggcaaacc ggcgtgcacc accctgctga actgcgcgaa ctttctgagc 1680
tgcctgtgca gcacctgcgc gctgtgccgc aaacgctag 1719

<210> SEQ ID NO 9
<211> LENGTH: 1677
<212> TYPE: DNA
<213> ORGANISM: Artificial Sequence
<220> FEATURE:
<223> OTHER INFORMATION: Influenza virus HA ectodomain fused T4 foldon sequence
<220> FEATURE:
<221> NAME/KEY: source
<222> LOCATION: (1)..(1677)
<223> OTHER INFORMATION: /mol_type="unassigned DNA" /note="Influenza virus HA ectodomain fused T4 foldon sequence" /organism="Artificial Sequence"

<400> SEQUENCE: 9
atgaaggcga tcctggtggt gctgctgtac acgttcgcga cggccaacgc ggatacgctg 60
tgcatcggct accacgcgaa caacagcacg gacaccgtgg acacggtgct cgagaagaac 120
gtgacggtga cgcacagcgt gaacctgctt gaggacaagc acaacggcaa gctgtgcaag 180
ctgcgtggcg tggctccgct gcacctgggc aagtgcaaca ttgctggctg gatcctgggc 240
aacccagagt gcgagagcct gagcacggcg tcgtcttgga gctacatcgt ggagacgccg 300
agcagcgaca acggcacgtg ctatccgggt gacttcatcg actacgaaga gctgcgcgag 360
cagctgtcgt cggtgagcag ctttgaacgc ttcgagattt tccccaagac gagcagctgg 420
ccgaaccacg actcgaacaa gggcgtgacg gctgcgtgtc cacacgctgg tgccaagagc 480
ttctacaaga acctgatctg gctggtgaag aagggcaaca gctacccgaa gctgagcaag 540
agctacatca acgacaaggg caaagaagtg ctcgtcctgt ggggcatcca ccacccgagc 600
acgagcgctg accagcagag cctgtaccag aacgccgaca cctacgtgtt cgtgggcagc 660
agccgctaca gcaagaagtt caagcccgag atcgcgattc gtccaaaggt gcgcgaccaa 720
gagggtcgca tgaactacta ctggacgctc gtggagccag gcgacaagat cacgttcgag 780
gcgacgggca acctggtcgt gccacgctac gccttcgcca tggaacgcaa cgctggcagc 840
ggcatcatca tcagcgacac gccagtgcac gactgcaaca cgacgtgcca gacgccgaag 900
ggtgcgatca acacgagcct gccgttccag aacatccacc cgatcacgat cggcaagtgc 960
ccgaagtacg tgaagagcac gaagctgcgc ctggcgacgg gtctgcgcaa catcccgagc 1020
atccagtctc gtggtctgtt tggcgctatc gctggcttca tcgagggtgg ctggacgggc 1080
atggtggacg gctggtacgg ctaccaccac cagaacgagc agggcagcgg ctacgctgcg 1140
gacctgaagt cgacgcagaa cgcgatcgac gagatcacga acaaggtgaa cagcgtgatc 1200

-continued gagaagatga acacgcagtt cacggctgtg ggcaaagagt tcaaccacct tgagaagcgc 1260
atcgagaacc tgaacaagaa ggtggacgac ggcttcctgg acatctggac gtacaacgcg 1320
gagctgctgg tgctgcttga gaacgagcgc acgctggact accacgattc gaacgtgaag 1380
aacctctacg agaaggtgcg cagccagctg aagaacaacg cgaaagagat cggcaacggc 1440
tgcttcgagt tctaccacaa gtgcgacaac acgtgcatgg aaagcgtgaa gaacggcacg 1500
tacgactacc cgaagtactc ggaagaggcc aagctgaacc gcgaagagat cgacggcgtg 1560
aagcttgaga gcacgcgcat ctaccagggc agcggctata ttccggaagc gccgcgcgat 1620
ggccaggcgt atgtgcgcaa agatggcgaa tgggtgctgc tgagcacctt tctgtag 1677

<210> SEQ ID NO 10
<211> LENGTH: 1587
<212> TYPE: DNA
<213> ORGANISM: Unknown
<220> FEATURE:
<223> OTHER INFORMATION: Influenza A virus
<220> FEATURE:
<221> NAME/KEY: source
<222> LOCATION: (1)..(1587)
<223> OTHER INFORMATION: /mol_type="unassigned DNA" /organism="Influenza A virus"

<400> SEQUENCE: 10
atgaaggcga tcctggtggt gctgctgtac acgttcgcga cggccaacgc ggatacgctg 60
tgcatcggct accacgcgaa caacagcacg gacaccgtgg acacggtgct cgagaagaac 120
gtgacggtga cgcacagcgt gaacctgctt gaggacaagc acaacggcaa gctgtgcaag 180
ctgcgtggcg tggctccgct gcacctgggc aagtgcaaca ttgctggctg gatcctgggc 240
aacccagagt gcgagagcct gagcacggcg tcgtcttgga gctacatcgt ggagacgccg 300
agcagcgaca acggcacgtg ctatccgggt gacttcatcg actacgaaga gctgcgcgag 360
cagctgtcgt cggtgagcag ctttgaacgc ttcgagattt tccccaagac gagcagctgg 420
ccgaaccacg actcgaacaa gggcgtgacg gctgcgtgtc cacacgctgg tgccaagagc 480
ttctacaaga acctgatctg gctggtgaag aagggcaaca gctacccgaa gctgagcaag 540
agctacatca acgacaaggg caaagaagtg ctcgtcctgt ggggcatcca ccacccgagc 600
acgagcgctg accagcagag cctgtaccag aacgccgaca cctacgtgtt cgtgggcagc 660
agccgctaca gcaagaagtt caagcccgag atcgcgattc gtccaaaggt gcgcgaccaa 720
gagggtcgca tgaactacta ctggacgctc gtggagccag gcgacaagat cacgttcgag 780
gcgacgggca acctggtcgt gccacgctac gccttcgcca tggaacgcaa cgctggcagc 840
ggcatcatca tcagcgacac gccagtgcac gactgcaaca cgacgtgcca gacgccgaag 900
ggtgcgatca acacgagcct gccgttccag aacatccacc cgatcacgat cggcaagtgc 960
ccgaagtacg tgaagagcac gaagctgcgc ctggcgacgg gtctgcgcaa catcccgagc 1020
atccagtctc gtggtctgtt tggcgctatc gctggcttca tcgagggtgg ctggacgggc 1080
atggtggacg gctggtacgg ctaccaccac cagaacgagc agggcagcgg ctacgctgcg 1140
gacctgaagt cgacgcagaa cgcgatcgac gagatcacga acaaggtgaa cagcgtgatc 1200
gagaagatga acacgcagtt cacggctgtg ggcaaagagt tcaaccacct tgagaagcgc 1260
atcgagaacc tgaacaagaa ggtggacgac ggcttcctgg acatctggac gtacaacgcg 1320
gagctgctgg tgctgcttga gaacgagcgc acgctggact accacgattc gaacgtgaag 1380
aacctctacg agaaggtgcg cagccagctg aagaacaacg cgaaagagat cggcaacggc 1440

```
tgcttcgagt tctaccacaa gtgcgacaac acgtgcatgg aaagcgtgaa gaacggcacg   1500

tacgactacc cgaagtactc ggaagaggcc aagctgaacc gcgaagagat cgacggcgtg   1560

aagcttgaga gcacgcgcat ctaccag                                       1587


<210> SEQ ID NO 11
<211> LENGTH: 529
<212> TYPE: PRT
<213> ORGANISM: Unknown
<220> FEATURE:
<223> OTHER INFORMATION: Influenza A virus

<400> SEQUENCE: 11

Met Lys Ala Ile Leu Val Val Leu Leu Tyr Thr Phe Ala Thr Ala Asn
1               5                   10                  15

Ala Asp Thr Leu Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Lys His Asn Gly Lys Leu Cys Lys Leu Arg Gly Val
    50                  55                  60

Ala Pro Leu His Leu Gly Lys Cys Asn Ile Ala Gly Trp Ile Leu Gly
65                  70                  75                  80

Asn Pro Glu Cys Glu Ser Leu Ser Thr Ala Ser Ser Trp Ser Tyr Ile
                85                  90                  95

Val Glu Thr Pro Ser Ser Asp Asn Gly Thr Cys Tyr Pro Gly Asp Phe
            100                 105                 110

Ile Asp Tyr Glu Glu Leu Arg Glu Gln Leu Ser Ser Val Ser Ser Phe
        115                 120                 125

Glu Arg Phe Glu Ile Phe Pro Lys Thr Ser Ser Trp Pro Asn His Asp
    130                 135                 140

Ser Asn Lys Gly Val Thr Ala Ala Cys Pro His Ala Gly Ala Lys Ser
145                 150                 155                 160

Phe Tyr Lys Asn Leu Ile Trp Leu Val Lys Lys Gly Asn Ser Tyr Pro
                165                 170                 175

Lys Leu Ser Lys Ser Tyr Ile Asn Asp Lys Gly Lys Glu Val Leu Val
            180                 185                 190

Leu Trp Gly Ile His His Pro Ser Thr Ser Ala Asp Gln Gln Ser Leu
        195                 200                 205

Tyr Gln Asn Ala Asp Thr Tyr Val Phe Val Gly Ser Ser Arg Tyr Ser
    210                 215                 220

Lys Lys Phe Lys Pro Glu Ile Ala Ile Arg Pro Lys Val Arg Asp Gln
225                 230                 235                 240

Glu Gly Arg Met Asn Tyr Tyr Trp Thr Leu Val Glu Pro Gly Asp Lys
                245                 250                 255

Ile Thr Phe Glu Ala Thr Gly Asn Leu Val Val Pro Arg Tyr Ala Phe
            260                 265                 270

Ala Met Glu Arg Asn Ala Gly Ser Gly Ile Ile Ile Ser Asp Thr Pro
        275                 280                 285

Val His Asp Cys Asn Thr Thr Cys Gln Thr Pro Lys Gly Ala Ile Asn
    290                 295                 300

Thr Ser Leu Pro Phe Gln Asn Ile His Pro Ile Thr Ile Gly Lys Cys
305                 310                 315                 320

Pro Lys Tyr Val Lys Ser Thr Lys Leu Arg Leu Ala Thr Gly Leu Arg
                325                 330                 335
```

-continued

```
Asn Ile Pro Ser Ile Gln Ser Arg Gly Leu Phe Gly Ala Ile Ala Gly
            340                 345                 350

Phe Ile Glu Gly Gly Trp Thr Gly Met Val Asp Gly Trp Tyr Gly Tyr
        355                 360                 365

His His Gln Asn Glu Gln Gly Ser Gly Tyr Ala Ala Asp Leu Lys Ser
    370                 375                 380

Thr Gln Asn Ala Ile Asp Glu Ile Thr Asn Lys Val Asn Ser Val Ile
385                 390                 395                 400

Glu Lys Met Asn Thr Gln Phe Thr Ala Val Gly Lys Glu Phe Asn His
                405                 410                 415

Leu Glu Lys Arg Ile Glu Asn Leu Asn Lys Lys Val Asp Asp Gly Phe
            420                 425                 430

Leu Asp Ile Trp Thr Tyr Asn Ala Glu Leu Leu Val Leu Leu Glu Asn
        435                 440                 445

Glu Arg Thr Leu Asp Tyr His Asp Ser Asn Val Lys Asn Leu Tyr Glu
    450                 455                 460

Lys Val Arg Ser Gln Leu Lys Asn Asn Ala Lys Glu Ile Gly Asn Gly
465                 470                 475                 480

Cys Phe Glu Phe Tyr His Lys Cys Asp Asn Thr Cys Met Glu Ser Val
                485                 490                 495

Lys Asn Gly Thr Tyr Asp Tyr Pro Lys Tyr Ser Glu Glu Ala Lys Leu
            500                 505                 510

Asn Arg Glu Glu Ile Asp Gly Val Lys Leu Glu Ser Thr Arg Ile Tyr
        515                 520                 525

Gln
```

<210> SEQ ID NO 12
<211> LENGTH: 1590
<212> TYPE: DNA
<213> ORGANISM: Unknown
<220> FEATURE:
<223> OTHER INFORMATION: Organism= Influenza A virus; Influenza virus HA ectodomain optimized for codon usage in CHO
<220> FEATURE:
<221> NAME/KEY: source
<222> LOCATION: (1)..(1590)
<223> OTHER INFORMATION: /mol_type="unassigned DNA" /note="Influenza virus HA ectodomain optimized for codon usage in CHO" /organism= "Influenza A virus"

<400> SEQUENCE: 12

```
atgaaggcca tcctggtggt gctgctgtac accttcgcca ccgccaacgc cgacaccctg     60

tgcatcggct accacgccaa caactccacc gacaccgtgg ataccgtgct ggaaaagaac    120

gtgaccgtga cccactccgt gaacctgctg gaagataagc acaacggcaa gctgtgcaag    180

ctgcggggcg tggcccctct gcacctgggc aagtgtaata tcgccggctg gatcctgggc    240

aaccccgagt gcgagtccct gtccaccgcc tccagctggt cctacatcgt ggaaaccccc    300

tccagcgaca acggcacctg ttaccccggc gacttcatcg actacgagga actgcgcgag    360

cagctgtcct ccgtgtccag cttcgagaga ttcgagatct tccccaagac ctcctcctgg    420

cccaaccacg actccaacaa gggcgtgacc gccgcctgtc ctcacgctgg cgccaagtcc    480

ttctacaaga acctgatctg gctggtgaaa aagggcaact cctaccccaa gctgtccaag    540

tcctacatca acgacaaggg caaagaggtg ctggtgctgt ggggcatcca ccaccccttcc    600

acctccgccg accagcagtc cctgtaccag aacgccgata cctacgtgtt cgtgggctcc    660

tcccggtact ccaagaagtt caagcccgag atcgccatcc ggcccaaagt gcgggaccag    720
```

-continued

```
gaaggccgga tgaactacta ctggaccctg gtggaacccg gcgacaagat caccttcgag    780
gccaccggca atctggtggt gcccagatac gccttcgcca tggaacggaa cgccggctcc    840
ggcatcatca tctccgacac ccccgtgcac gactgcaaca ccacctgtca gacccccaag    900
ggcgccatca acacctccct gcccttccag aacatccacc ccatcaccat cggcaagtgc    960
cccaaatacg tgaagtccac caagctgcgg ctggctaccg gcctgcggaa catcccctcc   1020
atccagtctc ggggcctgtt cggcgctatc gctggcttca tcgagggcgg ctggaccggc   1080
atggtggacg gttggtacgg ctaccaccac cagaacgagc agggctccgg ctacgccgcc   1140
gacctgaagt ctacccagaa cgccatcgac gagatcacca acaaagtgaa ctccgtgatc   1200
gagaagatga acacccagtt caccgccgtg ggcaaagagt tcaaccacct ggaaaagcgg   1260
atcgagaacc tgaacaagaa ggtggacgac ggcttcctgg acatctggac ctacaacgcc   1320
gagctgctgg tgctgctgga aaacgagcgg accctggact accacgacag caacgtgaag   1380
aacctgtacg agaaagtgcg gtcccagctg aagaacaacg ccaaagagat cggcaacggc   1440
tgcttcgagt tctaccacaa gtgcgacaac acctgtatgg aatccgtgaa gaacggcacc   1500
tacgactacc ccaagtactc cgaggaagcc aagctgaacc gggaagagat cgacggcgtg   1560
aagctggaat ccacccggat ctatcagtga                                    1590
```

<210> SEQ ID NO 13
<211> LENGTH: 1680
<212> TYPE: DNA
<213> ORGANISM: Artificial Sequence
<220> FEATURE:
<223> OTHER INFORMATION: Influenza virus HA ectodomain fused to lamprey multimerizing shortened sequence, optimized for codon usage in CHO
<220> FEATURE:
<221> NAME/KEY: source
<222> LOCATION: (1)..(1680)
<223> OTHER INFORMATION: /mol_type="unassigned DNA" /note="Influenza virus HA ectodomain fused to lamprey multimerizing shortened sequence, optimized for codon usage in CHO" /organism="Artificial Sequence"

<400> SEQUENCE: 13

```
atgaaggcca tcctggtggt gctgctgtac accttcgcca ccgccaacgc cgacaccctg     60
tgcatcggct accacgccaa caactccacc gacaccgtgg ataccgtgct ggaaaagaac    120
gtgaccgtga cccactccgt gaacctgctg gaagataagc acaacggcaa gctgtgcaag    180
ctgcggggcg tggcccctct gcacctgggc aagtgtaata tcgccggctg gatcctgggc    240
aaccccgagt gcgagtccct gtccaccgcc tccagctggt cctacatcgt ggaaaccccc    300
tccagcgaca acggcacctg ttaccccggc gacttcatcg actacgagga actgcgcgag    360
cagctgtcct ccgtgtccag cttcgagaga ttcgagatct tccccaagac ctcctcctgg    420
cccaaccacg actccaacaa gggcgtgacc gccgcctgtc ctcacgctgg cgccaagtcc    480
ttctacaaga acctgatctg gctggtgaaa aagggcaact cctaccccaa gctgtccaag    540
tcctacatca acgacaaggg caaagaggtg ctggtgctgt ggggcatcca ccacccttcc    600
acctccgccg accagcagtc cctgtaccag aacgccgata cctacgtgtt cgtgggctcc    660
tcccggtact ccaagaagtt caagcccgag atcgccatcc ggcccaaagt gcgggaccag    720
gaaggccgga tgaactacta ctggaccctg gtggaacccg gcgacaagat caccttcgag    780
gccaccggca atctggtggt gcccagatac gccttcgcca tggaacggaa cgccggctcc    840
ggcatcatca tctccgacac ccccgtgcac gactgcaaca ccacctgtca gacccccaag    900
```

-continued ggcgccatca acacctccct gcccttccag aacatccacc ccatcaccat cggcaagtgc 960
cccaaatacg tgaagtccac caagctgcgg ctggctaccg gcctgcggaa catcccctcc 1020
atccagtctc ggggcctgtt cggcgctatc gctggcttca tcgagggcgg ctggaccggc 1080
atggtggacg gttggtacgg ctaccaccac cagaacgagc agggctccgg ctacgccgcc 1140
gacctgaagt ctacccagaa cgccatcgac gagatcacca acaaagtgaa ctccgtgatc 1200
gagaagatga acacccagtt caccgccgtg ggcaaagagt tcaaccacct ggaaaagcgg 1260
atcgagaacc tgaacaagaa ggtggacgac ggcttcctgg acatctggac ctacaacgcc 1320
gagctgctgg tgctgctgga aaacgagcgg accctggact accacgacag caacgtgaag 1380
aacctgtacg agaaagtgcg gtcccagctg aagaacaacg ccaaagagat cggcaacggc 1440
tgcttcgagt tctaccacaa gtgcgacaac acctgtatgg aatccgtgaa gaacggcacc 1500
tacgactacc ccaagtactc cgaggaagcc aagctgaacc gggaagagat cgacggcgtg 1560
aagctggaat ccacccggat ctaccaggac tgcggcaagc ccgcctgcac caccctgctg 1620
aactgcgcca acttcctgtc ctgcctgtgc tctacctgcg ccctgtgccg gaagagatga 1680

<210> SEQ ID NO 14
<211> LENGTH: 1719
<212> TYPE: DNA
<213> ORGANISM: Artificial Sequence
<220> FEATURE:
<223> OTHER INFORMATION: Influenza virus HA ectodomain fused to lamprey multimerizing long sequence, optimized for codon usage in CHO
<220> FEATURE:
<221> NAME/KEY: source
<222> LOCATION: (1)..(1719)
<223> OTHER INFORMATION: /mol_type="unassigned DNA" /note="Influenza virus HA ectodomain fused to lamprey multimerizing long sequence, optimized for codon usage in CHO" /organism="Artificial Sequence"

<400> SEQUENCE: 14
atgaaggcca tcctggtggt gctgctgtac accttcgcca ccgccaacgc cgacaccctg 60
tgcatcggct accacgccaa caactccacc gacaccgtgg ataccgtgct ggaaaagaac 120
gtgaccgtga cccactccgt gaacctgctg gaagataagc acaacggcaa gctgtgcaag 180
ctgcggggcg tggcccctct gcacctgggc aagtgtaata tcgccggctg gatcctgggc 240
aaccccgagt gcgagtccct gtccaccgcc tccagctggt cctacatcgt ggaaaccccc 300
tccagcgaca acggcacctg ttaccccggc gacttcatcg actacgagga actgcgcgag 360
cagctgtcct ccgtgtccag cttcgagaga ttcgagatct tccccaagac ctcctcctgg 420
cccaaccacg actccaacaa gggcgtgacc gccgcctgtc ctcacgctgg cgccaagtcc 480
ttctacaaga acctgatctg gctggtgaaa aagggcaact cctaccccaa gctgtccaag 540
tcctacatca acgacaaggg caaagaggtg ctggtgctgt ggggcatcca ccaccccttcc 600 acctccgccg accagcagtc cctgtaccag aacgccgata cctacgtgtt cgtgggctcc 660
tcccggtact ccaagaagtt caagcccgag atcgccatcc ggcccaaagt gcgggaccag 720
gaaggccgga tgaactacta ctggaccctg gtggaacccg gcgacaagat caccttcgag 780
gccaccggca atctggtggt gcccagatac gccttcgcca tggaacggaa cgccggctcc 840
ggcatcatca tctccgacac ccccgtgcac gactgcaaca ccacctgtca gacccccaag 900
ggcgccatca acacctccct gcccttccag aacatccacc ccatcaccat cggcaagtgc 960
cccaaatacg tgaagtccac caagctgcgg ctggctaccg gcctgcggaa catcccctcc 1020
atccagtctc ggggcctgtt cggcgctatc gctggcttca tcgagggcgg ctggaccggc 1080
atggtggacg gttggtacgg ctaccaccac cagaacgagc agggctccgg ctacgccgcc 1140
gacctgaagt ctacccagaa cgccatcgac gagatcacca acaaagtgaa ctccgtgatc 1200
gagaagatga acacccagtt caccgccgtg ggcaaagagt tcaaccacct ggaaaagcgg 1260
atcgagaacc tgaacaagaa ggtggacgac ggcttcctgg acatctggac ctacaacgcc 1320
gagctgctgg tgctgctgga aaacgagcgg accctggact accacgacag caacgtgaag 1380
aacctgtacg agaaagtgcg gtcccagctg aagaacaacg ccaaagagat cggcaacggc 1440
tgcttcgagt tctaccacaa gtgcgacaac acctgtatgg aatccgtgaa gaacggcacc 1500
tacgactacc ccaagtactc cgaggaagcc aagctgaacc gggaagagat cgacggcgtg 1560
aagctggaat ccacccggat ctaccagaac tgcaccagca tccaggaacg gaagaacgac 1620
ggcggcgact gcggcaagcc tgcctgcacc accctgctga actgcgccaa cttcctgtcc 1680
tgcctgtgct ctacctgcgc cctgtgccgg aagagatga 1719

<210> SEQ ID NO 15
<211> LENGTH: 1677
<212> TYPE: DNA
<213> ORGANISM: Artificial Sequence
<220> FEATURE:
<223> OTHER INFORMATION: Influenza virus HA ectodomain fused to T4 foldon multimerizing sequence, optimized for codon usage in CHO
<220> FEATURE:
<221> NAME/KEY: source
<222> LOCATION: (1)..(1677)
<223> OTHER INFORMATION: /mol_type="unassigned DNA" /note="Influenza virus HA ectodomain fused to T4 foldon multimerizing sequence, optimized for codon usage in CHO" /organism="Artificial Sequence"

<400> SEQUENCE: 15
atgaaggcca tcctggtggt gctgctgtac accttcgcca ccgccaacgc cgacaccctg 60
tgcatcggct accacgccaa caactccacc gacaccgtgg ataccgtgct ggaaaagaac 120
gtgaccgtga cccactccgt gaacctgctg gaagataagc acaacggcaa gctgtgcaag 180
ctgcggggcg tggcccctct gcacctgggc aagtgtaata tcgccggctg gatcctgggc 240
aaccccgagt gcgagtccct gtccaccgcc tccagctggt cctacatcgt ggaaaccccc 300
tccagcgaca acggcacctg ttaccccggc gacttcatcg actacgagga actgcgcgag 360
cagctgtcct ccgtgtccag cttcgagaga ttcgagatct tccccaagac ctcctcctgg 420
cccaaccacg actccaacaa gggcgtgacc gccgcctgtc ctcacgctgg cgccaagtcc 480
ttctacaaga acctgatctg gctggtgaaa aagggcaact cctaccccaa gctgtccaag 540
tcctacatca acgacaaggg caaagaggtg ctggtgctgt ggggcatcca ccaccccttcc 600 acctccgccg accagcagtc cctgtaccag aacgccgata cctacgtgtt cgtgggctcc 660
tcccggtact ccaagaagtt caagcccgag atcgccatcc ggcccaaagt gcgggaccag 720
gaaggccgga tgaactacta ctggaccctg gtggaacccg gcgacaagat caccttcgag 780
gccaccggca atctggtggt gcccagatac gccttcgcca tggaacggaa cgccggctcc 840
ggcatcatca tctccgacac ccccgtgcac gactgcaaca ccacctgtca gacccccaag 900
ggcgccatca acacctccct gcccttccag aacatccacc ccatcaccat cggcaagtgc 960
cccaaatacg tgaagtccac caagctgcgg ctggctaccg gcctgcggaa catcccctcc 1020
atccagtctc ggggcctgtt cggcgctatc gctggcttca tcgagggcgg ctggaccggc 1080
atggtggacg gttggtacgg ctaccaccac cagaacgagc agggctccgg ctacgccgcc 1140
gacctgaagt ctacccagaa cgccatcgac gagatcacca acaaagtgaa ctccgtgatc 1200

-continued gagaagatga acacccagtt caccgccgtg ggcaaagagt tcaaccacct ggaaaagcgg 1260
atcgagaacc tgaacaagaa ggtggacgac ggcttcctgg acatctggac ctacaacgcc 1320
gagctgctgg tgctgctgga aaacgagcgg accctggact accacgacag caacgtgaag 1380
aacctgtacg agaaagtgcg gtcccagctg aagaacaacg ccaaagagat cggcaacggc 1440
tgcttcgagt tctaccacaa gtgcgacaac acctgtatgg aatccgtgaa gaacggcacc 1500
tacgactacc ccaagtactc cgaggaagcc aagctgaacc gggaagagat cgacggcgtg 1560
aagctggaat ccacccggat ctaccagggc agcggctaca tccctgaggc ccccagagat 1620
ggccaggcct acgtgcggaa ggacggcgag tgggtgctgc tgagcacatt tctgtga 1677

<210> SEQ ID NO 16
<211> LENGTH: 996
<212> TYPE: DNA
<213> ORGANISM: Unknown
<220> FEATURE:
<223> OTHER INFORMATION: Organism= Shigella flexneri 2a str. 301; IpaD sequence optimized for codon usage in E. coli
<220> FEATURE:
<221> NAME/KEY: source
<222> LOCATION: (1)..(996)
<223> OTHER INFORMATION: /mol_type="unassigned DNA" /note="IpaD sequence optimized for codon usage in E. coli" /organism="Shigella flexneri 2a str. 301"

<400> SEQUENCE: 16
atgaatatta ccaccctgac caatagcatt agcaccagca gctttagccc gaataatacc 60
aatggtagca gcaccgaaac cgttaatagc gatattaaaa ccaccacctc tagccatccg 120
gttagcagcc tgaccatgct gaatgatacc ctgcataata ttcgtaccac caatcaggca 180
ctgaaaaaag aactgagcca gaaaaccctg accaaaacca gcctggaaga aattgcactg 240
catagcagcc agattagcat ggatgttaat aaaagcgcac agctgctgga tattctgtct 300
cgccatgaat atccgattaa taaagatgca cgcgaactgc tgcatagcgc accgaaagaa 360
gcagaactgg acggcgatca gatgattagc catcgtgaac tgtgggcaaa aattgcgaat 420
agcattaatg atattaatga acagtatctg aaagtgtatg aacatgccgt tagcagctat 480
acccagatgt atcaggattt ttctgccgtt ttaagctctc tggctggctg gatttctccg 540
ggtggtaatg atggtaatag cgtgaaactg caggttaata gcctgaaaaa agccctggaa 600
gaactgaaag aaaaatataa agataaaccg ctgtatccgg ctaataatac cgttagccaa 660
gaacaggcaa ataaatggct gaccgaactg ggtggcacca ttggtaaagt gtctcagaaa 720
aatggtggtt atgtggtgag cattaatatg accccgattg ataatatgct gaaaagcctg 780
gataatctgg gtggtaatgg tgaagttgtt ctggataatg ccaaatatca ggcatggaat 840
gccggtttta gcgccgaaga tgaaaccatg aaaaataatc tgcagaccct ggttcagaaa 900
tatagcaatg ccaatagcat ttttgataat ctggtgaaag ttctgtctag caccattagc 960
agctgtaccg ataccgataa actgtttctg catttt 996

<210> SEQ ID NO 17
<211> LENGTH: 1125
<212> TYPE: DNA
<213> ORGANISM: Artificial Sequence
<220> FEATURE:
<223> OTHER INFORMATION: Shigella IpaD fused to lamprey multimerizing long sequence, optimized for codon usage in E. coli
<220> FEATURE:
<221> NAME/KEY: source
<222> LOCATION: (1)..(1125)
<223> OTHER INFORMATION: /mol_type="unassigned DNA" /note="Shigella IpaD -continued fused to lamprey multimerizing long sequence, optimized for codon usage in E. coli" /organism="Artificial Sequence"

<400> SEQUENCE: 17

```
atgaatatta ccaccctgac caatagcatt agcaccagca gctttagccc gaataatacc     60

aatggtagca gcaccgaaac cgttaatagc gatattaaaa ccaccacctc tagccatccg    120

gttagcagcc tgaccatgct gaatgatacc ctgcataata ttcgtaccac caatcaggca    180

ctgaaaaaag aactgagcca gaaaaccctg accaaaacca gcctggaaga aattgcactg    240

catagcagcc agattagcat ggatgttaat aaaagcgcac agctgctgga tattctgtct    300

cgccatgaat atccgattaa taaagatgca cgcgaactgc tgcatagcgc accgaaagaa    360

gcagaactgg acggcgatca gatgattagc catcgtgaac tgtgggcaaa aattgcgaat    420

agcattaatg atattaatga acagtatctg aaagtgtatg aacatgccgt tagcagctat    480

acccagatgt atcaggattt ttctgccgtt ttaagctctc tggctggctg gatttctccg    540

ggtggtaatg atggtaatag cgtgaaactg caggttaata gcctgaaaaa agccctggaa    600

gaactgaaag aaaaatataa agataaaccg ctgtatccgg ctaataatac cgttagccaa    660

gaacaggcaa ataaatggct gaccgaactg ggtggcacca ttggtaaagt gtctcagaaa    720

aatggtggtt atgtggtgag cattaatatg accccgattg ataatatgct gaaaagcctg    780

gataatctgg gtggtaatgg tgaagttgtt ctggataatg ccaaatatca ggcatggaat    840

gccggtttta gcgccgaaga tgaaaccatg aaaaataatc tgcagaccct ggttcagaaa    900

tatagcaatg ccaatagcat ttttgataat ctggtgaaag ttctgtctag caccattagc    960

agctgtaccg ataccgataa actgtttctg cattttaatt gtaccagcat tcaagagcgc   1020

aaaaatgatg gtggtgattg tggtaaaccg gcatgtacca ccctgctgaa ttgtgcaaat   1080

tttctgagct gtctgtgtag cacctgtgca ctgtgtcgta aacgt                   1125
```

<210> SEQ ID NO 18
<211> LENGTH: 375
<212> TYPE: PRT
<213> ORGANISM: Artificial Sequence
<220> FEATURE:
<223> OTHER INFORMATION: Shigella IpaD fused to lamprey multimerizing long sequence

<400> SEQUENCE: 18

```
Met Asn Ile Thr Thr Leu Thr Asn Ser Ile Ser Thr Ser Ser Phe Ser
1               5                   10                  15

Pro Asn Asn Thr Asn Gly Ser Ser Thr Glu Thr Val Asn Ser Asp Ile
            20                  25                  30

Lys Thr Thr Thr Ser Ser His Pro Val Ser Ser Leu Thr Met Leu Asn
        35                  40                  45

Asp Thr Leu His Asn Ile Arg Thr Thr Asn Gln Ala Leu Lys Lys Glu
    50                  55                  60

Leu Ser Gln Lys Thr Leu Thr Lys Thr Ser Leu Glu Glu Ile Ala Leu
65                  70                  75                  80

His Ser Ser Gln Ile Ser Met Asp Val Asn Lys Ser Ala Gln Leu Leu
                85                  90                  95

Asp Ile Leu Ser Arg His Glu Tyr Pro Ile Asn Lys Asp Ala Arg Glu
            100                 105                 110

Leu Leu His Ser Ala Pro Lys Glu Ala Glu Leu Asp Gly Asp Gln Met
        115                 120                 125

Ile Ser His Arg Glu Leu Trp Ala Lys Ile Ala Asn Ser Ile Asn Asp
```

```
    130                 135                 140

Ile Asn Glu Gln Tyr Leu Lys Val Tyr Glu His Ala Val Ser Ser Tyr
145                 150                 155                 160

Thr Gln Met Tyr Gln Asp Phe Ser Ala Val Leu Ser Ser Leu Ala Gly
                165                 170                 175

Trp Ile Ser Pro Gly Gly Asn Asp Gly Asn Ser Val Lys Leu Gln Val
            180                 185                 190

Asn Ser Leu Lys Lys Ala Leu Glu Glu Leu Lys Glu Lys Tyr Lys Asp
        195                 200                 205

Lys Pro Leu Tyr Pro Ala Asn Asn Thr Val Ser Gln Glu Gln Ala Asn
    210                 215                 220

Lys Trp Leu Thr Glu Leu Gly Gly Thr Ile Gly Lys Val Ser Gln Lys
225                 230                 235                 240

Asn Gly Gly Tyr Val Val Ser Ile Asn Met Thr Pro Ile Asp Asn Met
                245                 250                 255

Leu Lys Ser Leu Asp Asn Leu Gly Gly Asn Gly Glu Val Val Leu Asp
            260                 265                 270

Asn Ala Lys Tyr Gln Ala Trp Asn Ala Gly Phe Ser Ala Glu Asp Glu
        275                 280                 285

Thr Met Lys Asn Asn Leu Gln Thr Leu Val Gln Lys Tyr Ser Asn Ala
    290                 295                 300

Asn Ser Ile Phe Asp Asn Leu Val Lys Val Leu Ser Ser Thr Ile Ser
305                 310                 315                 320

Ser Cys Thr Asp Thr Asp Lys Leu Phe Leu His Phe Asn Cys Thr Ser
                325                 330                 335

Ile Gln Glu Arg Lys Asn Asp Gly Gly Asp Cys Gly Lys Pro Ala Cys
            340                 345                 350

Thr Thr Leu Leu Asn Cys Ala Asn Phe Leu Ser Cys Leu Cys Ser Thr
        355                 360                 365

Cys Ala Leu Cys Arg Lys Arg
    370                 375
```

<210> SEQ ID NO 19
<211> LENGTH: 1032
<212> TYPE: DNA
<213> ORGANISM: Artificial Sequence
<220> FEATURE:
<223> OTHER INFORMATION: Shigella IpaD fused to a His-tag, optimized for codon usage in E. coli
<220> FEATURE:
<221> NAME/KEY: source
<222> LOCATION: (1)..(1032)
<223> OTHER INFORMATION: /mol_type="unassigned DNA" /note="Shigella IpaD fused to a His-tag, optimized for codon usage in E. coli" /organism="Artificial Sequence"

<400> SEQUENCE: 19

```
atgaatatta ccaccctgac caatagcatt agcaccagca gctttagccc gaataatacc      60

aatggtagca gcaccgaaac cgttaatagc gatattaaaa ccaccacctc tagccatccg     120

gttagcagcc tgaccatgct gaatgatacc ctgcataata ttcgtaccac caatcaggca     180

ctgaaaaaag aactgagcca gaaaaccctg accaaaacca gcctggaaga aattgcactg     240

catagcagcc agattagcat ggatgttaat aaaagcgcac agctgctgga tattctgtct     300

cgccatgaat atccgattaa taaagatgca cgcgaactgc tgcatagcgc accgaaagaa     360

gcagaactgg acggcgatca gatgattagc catcgtgaac tgtgggcaaa aattgcgaat     420

agcattaatg atattaatga acagtatctg aaagtgtatg aacatgccgt tagcagctat     480
```

acccagatgt atcaggattt ttctgccgtt ttaagctctc tggctggctg gatttctccg 540
ggtggtaatg atggtaatag cgtgaaactg caggttaata gcctgaaaaa agccctggaa 600
gaactgaaag aaaaatataa agataaaccg ctgtatccgg ctaataatac cgttagccaa 660
gaacaggcaa ataaatggct gaccgaactg ggtggcacca ttggtaaagt gtctcagaaa 720
aatggtggtt atgtggtgag cattaatatg accccgattg ataatatgct gaaaagcctg 780
gataatctgg gtggtaatgg tgaagttgtt ctggataatg ccaaatatca ggcatggaat 840
gccggtttta gcgccgaaga tgaaaccatg aaaaataatc tgcagaccct ggttcagaaa 900
tatagcaatg ccaatagcat ttttgataat ctggtgaaag ttctgtctag caccattagc 960
agctgtaccg ataccgataa actgtttctg cattttggtg gtagcctcga gcaccaccac 1020
caccaccact ga 1032

<210> SEQ ID NO 20
<211> LENGTH: 1158
<212> TYPE: DNA
<213> ORGANISM: Artificial Sequence
<220> FEATURE:
<223> OTHER INFORMATION: Shigella IpaD fused to lamprey multimerizing long sequence and to a His-tag, optimized for codon usage in E. coli
<220> FEATURE:
<221> NAME/KEY: source
<222> LOCATION: (1)..(1158)
<223> OTHER INFORMATION: /mol_type="unassigned DNA" /note="Shigella IpaD fused to lamprey multimerizing long sequence and to a His-tag, optimized for codon usage in E. coli" /organism="Artificial Sequence"

<400> SEQUENCE: 20
atgaatatta ccaccctgac caatagcatt agcaccagca gctttagccc gaataatacc 60
aatggtagca gcaccgaaac cgttaatagc gatattaaaa ccaccacctc tagccatccg 120
gttagcagcc tgaccatgct gaatgatacc ctgcataata ttcgtaccac caatcaggca 180
ctgaaaaaag aactgagcca gaaaaccctg accaaaacca gcctggaaga aattgcactg 240
catagcagcc agattagcat ggatgttaat aaaagcgcac agctgctgga tattctgtct 300
cgccatgaat atccgattaa taaagatgca cgcgaactgc tgcatagcgc accgaaagaa 360
gcagaactgg acggcgatca gatgattagc catcgtgaac tgtgggcaaa aattgcgaat 420
agcattaatg atattaatga acagtatctg aaagtgtatg aacatgccgt tagcagctat 480
acccagatgt atcaggattt ttctgccgtt ttaagctctc tggctggctg gatttctccg 540
ggtggtaatg atggtaatag cgtgaaactg caggttaata gcctgaaaaa agccctggaa 600
gaactgaaag aaaaatataa agataaaccg ctgtatccgg ctaataatac cgttagccaa 660
gaacaggcaa ataaatggct gaccgaactg ggtggcacca ttggtaaagt gtctcagaaa 720
aatggtggtt atgtggtgag cattaatatg accccgattg ataatatgct gaaaagcctg 780
gataatctgg gtggtaatgg tgaagttgtt ctggataatg ccaaatatca ggcatggaat 840
gccggtttta gcgccgaaga tgaaaccatg aaaaataatc tgcagaccct ggttcagaaa 900
tatagcaatg ccaatagcat ttttgataat ctggtgaaag ttctgtctag caccattagc 960
agctgtaccg ataccgataa actgtttctg cattttaatt gtaccagcat tcaagagcgc 1020
aaaaatgatg gtggtgattg tggtaaaccg gcatgtacca ccctgctgaa ttgtgcaaat 1080
tttctgagct gtctgtgtag cacctgtgca ctgtgtcgta aacgtggtgg tagcctcgag 1140
caccaccacc accaccac 1158

-continued

<210> SEQ ID NO 21
<211> LENGTH: 249
<212> TYPE: DNA
<213> ORGANISM: Artificial Sequence
<220> FEATURE:
<223> OTHER INFORMATION: Organism= Shigella flexneri 2a str. 301; MxiH sequence, optimized for codon usage in E. coli
<220> FEATURE:
<221> NAME/KEY: source
<222> LOCATION: (1)..(249)
<223> OTHER INFORMATION: /mol_type="unassigned DNA" /note="MxiH sequence, optimized for codon usage in E. coli" /organism= "Shigella flexneri 2a str. 301"

<400> SEQUENCE: 21

```
atgagtgtta ccgttccgaa tgatgattgg accctgagca gcctgagcga aacctttgat     60

gatggcaccc agacactgca gggtgaactg accctggcac tggataaact ggcaaaaaat    120

ccgagcaatc cgcagctgct ggcagaatat cagagcaaac tgagcgaata taccctgtat    180

cgtaatgcac agagcaatac cgtgaaagtg attaaagatg ttgatgcagc catcatccag    240

aactttcgt                                                            249
```

<210> SEQ ID NO 22
<211> LENGTH: 378
<212> TYPE: DNA
<213> ORGANISM: Artificial Sequence
<220> FEATURE:
<223> OTHER INFORMATION: Shigella MxiH fused to lamprey multimerizing long sequence, optimized for codon usage in E. coli
<220> FEATURE:
<221> NAME/KEY: source
<222> LOCATION: (1)..(378)
<223> OTHER INFORMATION: /mol_type="unassigned DNA" /note="Shigella MxiH fused to lamprey multimerizing long sequence, optimized for codon usage in E. coli" /organism="Artificial Sequence"

<400> SEQUENCE: 22

```
atgagcgtta ccgttccgaa tgatgattgg accctgagca gcctgagcga aacctttgat     60

gatggcaccc agacactgca gggtgaactg accctggcac tggataaact ggcaaaaaat    120

ccgagcaatc cgcagctgct ggcagaatat cagagcaaac tgagcgaata taccctgtat    180

cgtaatgcac agagcaatac cgtgaaagtg attaaagatg ttgatgcagc catcatccag    240

aattttcgta attgtaccag catccaagag cgcaaaaatg atggtggtga ttgtggtaaa    300

ccggcatgta ccaccctgct gaattgtgca aattttctga gctgtctgtg tagcacctgt    360

gcactgtgtc gtaaacgt                                                  378
```

<210> SEQ ID NO 23
<211> LENGTH: 126
<212> TYPE: PRT
<213> ORGANISM: Artificial Sequence
<220> FEATURE:
<223> OTHER INFORMATION: Shigella MxiH fused to lamprey multimerizing long sequence

<400> SEQUENCE: 23

```
Met Ser Val Thr Val Pro Asn Asp Asp Trp Thr Leu Ser Ser Leu Ser
1               5                   10                  15

Glu Thr Phe Asp Asp Gly Thr Gln Thr Leu Gln Gly Glu Leu Thr Leu
            20                  25                  30

Ala Leu Asp Lys Leu Ala Lys Asn Pro Ser Asn Pro Gln Leu Leu Ala
        35                  40                  45
```

-continued

```
Glu Tyr Gln Ser Lys Leu Ser Glu Tyr Thr Leu Tyr Arg Asn Ala Gln
    50                  55                  60

Ser Asn Thr Val Lys Val Ile Lys Asp Val Asp Ala Ala Ile Ile Gln
65                  70                  75                  80

Asn Phe Arg Asn Cys Thr Ser Ile Gln Glu Arg Lys Asn Asp Gly Gly
                85                  90                  95

Asp Cys Gly Lys Pro Ala Cys Thr Thr Leu Leu Asn Cys Ala Asn Phe
            100                 105                 110

Leu Ser Cys Leu Cys Ser Thr Cys Ala Leu Cys Arg Lys Arg
        115                 120                 125


<210> SEQ ID NO 24
<211> LENGTH: 282
<212> TYPE: DNA
<213> ORGANISM: Artificial Sequence
<220> FEATURE:
<223> OTHER INFORMATION: Shigella MxiH fused to a His-tag, optimized for
      codon usage in E. coli
<220> FEATURE:
<221> NAME/KEY: source
<222> LOCATION: (1)..(282)
<223> OTHER INFORMATION: /mol_type="unassigned DNA" /note="Shigella MxiH
      fused to a His-tag, optimized for codon usage in E. coli"
      /organism="Artificial Sequence"

<400> SEQUENCE: 24

atgagtgtta ccgttccgaa tgatgattgg accctgagca gcctgagcga aacctttgat      60

gatggcaccc agacactgca gggtgaactg accctggcac tggataaact ggcaaaaaat     120

ccgagcaatc cgcagctgct ggcagaatat cagagcaaac tgagcgaata taccctgtat     180

cgtaatgcac agagcaatac cgtgaaagtg attaaagatg ttgatgcagc catcatccag     240

aattttcgtg gtggtagcct cgagcaccac caccaccacc ac                        282


<210> SEQ ID NO 25
<211> LENGTH: 411
<212> TYPE: DNA
<213> ORGANISM: Artificial Sequence
<220> FEATURE:
<223> OTHER INFORMATION: Shigella MxiH fused to lamprey multimerizing
      long sequence and to a His-tag, optimized for codon usage in E.
      coli
<220> FEATURE:
<221> NAME/KEY: source
<222> LOCATION: (1)..(411)
<223> OTHER INFORMATION: /mol_type="unassigned DNA" /note="Shigella MxiH
      fused to lamprey multimerizing long sequence and to a His-tag,
      optimized for codon usage in E. coli" /organism="Artificial
      Sequence"

<400> SEQUENCE: 25

atgagtgtta ccgttccgaa tgatgattgg accctgagca gcctgagcga aacctttgat      60

gatggcaccc agacactgca gggtgaactg accctggcac tggataaact ggcaaaaaat     120

ccgagcaatc cgcagctgct ggcagaatat cagagcaaac tgagcgaata taccctgtat     180

cgtaatgcac agagcaatac cgtgaaagtg attaaagatg ttgatgcagc catcatccag     240

aattttcgta attgtaccag catccaagag cgcaaaaatg atggtggtga ttgtggtaaa     300

ccggcatgta ccaccctgct gaattgtgca aattttctga gctgtctgtg tagcacctgt     360

gcactgtgtc gtaaacgtgg tggtagcctc gagcaccacc accaccacca c              411


<210> SEQ ID NO 26
<211> LENGTH: 559
<212> TYPE: PRT
```

<213> ORGANISM: Artificial Sequence
<220> FEATURE:
<223> OTHER INFORMATION: Influenza virus HA ectodomain fused to lamprey multimerizing shortened sequence

<400> SEQUENCE: 26

```
Met Lys Ala Ile Leu Val Val Leu Leu Tyr Thr Phe Ala Thr Ala Asn
1               5                   10                  15

Ala Asp Thr Leu Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Lys His Asn Gly Lys Leu Cys Lys Leu Arg Gly Val
    50                  55                  60

Ala Pro Leu His Leu Gly Lys Cys Asn Ile Ala Gly Trp Ile Leu Gly
65                  70                  75                  80

Asn Pro Glu Cys Glu Ser Leu Ser Thr Ala Ser Ser Trp Ser Tyr Ile
                85                  90                  95

Val Glu Thr Pro Ser Ser Asp Asn Gly Thr Cys Tyr Pro Gly Asp Phe
            100                 105                 110

Ile Asp Tyr Glu Glu Leu Arg Glu Gln Leu Ser Ser Val Ser Ser Phe
        115                 120                 125

Glu Arg Phe Glu Ile Phe Pro Lys Thr Ser Ser Trp Pro Asn His Asp
    130                 135                 140

Ser Asn Lys Gly Val Thr Ala Ala Cys Pro His Ala Gly Ala Lys Ser
145                 150                 155                 160

Phe Tyr Lys Asn Leu Ile Trp Leu Val Lys Lys Gly Asn Ser Tyr Pro
                165                 170                 175

Lys Leu Ser Lys Ser Tyr Ile Asn Asp Lys Gly Lys Glu Val Leu Val
            180                 185                 190

Leu Trp Gly Ile His His Pro Ser Thr Ser Ala Asp Gln Gln Ser Leu
        195                 200                 205

Tyr Gln Asn Ala Asp Thr Tyr Val Phe Val Gly Ser Ser Arg Tyr Ser
    210                 215                 220

Lys Lys Phe Lys Pro Glu Ile Ala Ile Arg Pro Lys Val Arg Asp Gln
225                 230                 235                 240

Glu Gly Arg Met Asn Tyr Tyr Trp Thr Leu Val Glu Pro Gly Asp Lys
                245                 250                 255

Ile Thr Phe Glu Ala Thr Gly Asn Leu Val Val Pro Arg Tyr Ala Phe
            260                 265                 270

Ala Met Glu Arg Asn Ala Gly Ser Gly Ile Ile Ile Ser Asp Thr Pro
        275                 280                 285

Val His Asp Cys Asn Thr Thr Cys Gln Thr Pro Lys Gly Ala Ile Asn
    290                 295                 300

Thr Ser Leu Pro Phe Gln Asn Ile His Pro Ile Thr Ile Gly Lys Cys
305                 310                 315                 320

Pro Lys Tyr Val Lys Ser Thr Lys Leu Arg Leu Ala Thr Gly Leu Arg
                325                 330                 335

Asn Ile Pro Ser Ile Gln Ser Arg Gly Leu Phe Gly Ala Ile Ala Gly
            340                 345                 350

Phe Ile Glu Gly Gly Trp Thr Gly Met Val Asp Gly Trp Tyr Gly Tyr
        355                 360                 365

His His Gln Asn Glu Gln Gly Ser Gly Tyr Ala Ala Asp Leu Lys Ser
    370                 375                 380
```

-continued

```
Thr Gln Asn Ala Ile Asp Glu Ile Thr Asn Lys Val Asn Ser Val Ile
385                 390                 395                 400

Glu Lys Met Asn Thr Gln Phe Thr Ala Val Gly Lys Glu Phe Asn His
                405                 410                 415

Leu Glu Lys Arg Ile Glu Asn Leu Asn Lys Lys Val Asp Asp Gly Phe
            420                 425                 430

Leu Asp Ile Trp Thr Tyr Asn Ala Glu Leu Leu Val Leu Leu Glu Asn
        435                 440                 445

Glu Arg Thr Leu Asp Tyr His Asp Ser Asn Val Lys Asn Leu Tyr Glu
    450                 455                 460

Lys Val Arg Ser Gln Leu Lys Asn Asn Ala Lys Glu Ile Gly Asn Gly
465                 470                 475                 480

Cys Phe Glu Phe Tyr His Lys Cys Asp Asn Thr Cys Met Glu Ser Val
                485                 490                 495

Lys Asn Gly Thr Tyr Asp Tyr Pro Lys Tyr Ser Glu Glu Ala Lys Leu
            500                 505                 510

Asn Arg Glu Glu Ile Asp Gly Val Lys Leu Glu Ser Thr Arg Ile Tyr
        515                 520                 525

Gln Asp Cys Gly Lys Pro Ala Cys Thr Thr Leu Leu Asn Cys Ala Asn
    530                 535                 540

Phe Leu Ser Cys Leu Cys Ser Thr Cys Ala Leu Cys Arg Lys Arg
545                 550                 555
```

```
<210> SEQ ID NO 27
<211> LENGTH: 572
<212> TYPE: PRT
<213> ORGANISM: Artificial Sequence
<220> FEATURE:
<223> OTHER INFORMATION: Influenza virus HA ectodomain fused to lamprey
      multimerizing long sequence

<400> SEQUENCE: 27

Met Lys Ala Ile Leu Val Val Leu Leu Tyr Thr Phe Ala Thr Ala Asn
1               5                   10                  15

Ala Asp Thr Leu Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Lys His Asn Gly Lys Leu Cys Lys Leu Arg Gly Val
    50                  55                  60

Ala Pro Leu His Leu Gly Lys Cys Asn Ile Ala Gly Trp Ile Leu Gly
65                  70                  75                  80

Asn Pro Glu Cys Glu Ser Leu Ser Thr Ala Ser Ser Trp Ser Tyr Ile
                85                  90                  95

Val Glu Thr Pro Ser Ser Asp Asn Gly Thr Cys Tyr Pro Gly Asp Phe
            100                 105                 110

Ile Asp Tyr Glu Glu Leu Arg Glu Gln Leu Ser Ser Val Ser Ser Phe
        115                 120                 125

Glu Arg Phe Glu Ile Phe Pro Lys Thr Ser Ser Trp Pro Asn His Asp
    130                 135                 140

Ser Asn Lys Gly Val Thr Ala Ala Cys Pro His Ala Gly Ala Lys Ser
145                 150                 155                 160

Phe Tyr Lys Asn Leu Ile Trp Leu Val Lys Lys Gly Asn Ser Tyr Pro
                165                 170                 175

Lys Leu Ser Lys Ser Tyr Ile Asn Asp Lys Gly Lys Glu Val Leu Val
            180                 185                 190
```

-continued

```
Leu Trp Gly Ile His His Pro Ser Thr Ser Ala Asp Gln Gln Ser Leu
        195                 200                 205

Tyr Gln Asn Ala Asp Thr Tyr Val Phe Val Gly Ser Ser Arg Tyr Ser
    210                 215                 220

Lys Lys Phe Lys Pro Glu Ile Ala Ile Arg Pro Lys Val Arg Asp Gln
225                 230                 235                 240

Glu Gly Arg Met Asn Tyr Tyr Trp Thr Leu Val Glu Pro Gly Asp Lys
                245                 250                 255

Ile Thr Phe Glu Ala Thr Gly Asn Leu Val Val Pro Arg Tyr Ala Phe
            260                 265                 270

Ala Met Glu Arg Asn Ala Gly Ser Gly Ile Ile Ile Ser Asp Thr Pro
        275                 280                 285

Val His Asp Cys Asn Thr Thr Cys Gln Thr Pro Lys Gly Ala Ile Asn
    290                 295                 300

Thr Ser Leu Pro Phe Gln Asn Ile His Pro Ile Thr Ile Gly Lys Cys
305                 310                 315                 320

Pro Lys Tyr Val Lys Ser Thr Lys Leu Arg Leu Ala Thr Gly Leu Arg
                325                 330                 335

Asn Ile Pro Ser Ile Gln Ser Arg Gly Leu Phe Gly Ala Ile Ala Gly
            340                 345                 350

Phe Ile Glu Gly Gly Trp Thr Gly Met Val Asp Gly Trp Tyr Gly Tyr
        355                 360                 365

His His Gln Asn Glu Gln Gly Ser Gly Tyr Ala Ala Asp Leu Lys Ser
    370                 375                 380

Thr Gln Asn Ala Ile Asp Glu Ile Thr Asn Lys Val Asn Ser Val Ile
385                 390                 395                 400

Glu Lys Met Asn Thr Gln Phe Thr Ala Val Gly Lys Glu Phe Asn His
                405                 410                 415

Leu Glu Lys Arg Ile Glu Asn Leu Asn Lys Lys Val Asp Asp Gly Phe
            420                 425                 430

Leu Asp Ile Trp Thr Tyr Asn Ala Glu Leu Leu Val Leu Leu Glu Asn
        435                 440                 445

Glu Arg Thr Leu Asp Tyr His Asp Ser Asn Val Lys Asn Leu Tyr Glu
    450                 455                 460

Lys Val Arg Ser Gln Leu Lys Asn Asn Ala Lys Glu Ile Gly Asn Gly
465                 470                 475                 480

Cys Phe Glu Phe Tyr His Lys Cys Asp Asn Thr Cys Met Glu Ser Val
                485                 490                 495

Lys Asn Gly Thr Tyr Asp Tyr Pro Lys Tyr Ser Glu Glu Ala Lys Leu
            500                 505                 510

Asn Arg Glu Glu Ile Asp Gly Val Lys Leu Glu Ser Thr Arg Ile Tyr
        515                 520                 525

Gln Asn Cys Thr Ser Ile Gln Glu Arg Lys Asn Asp Gly Gly Asp Cys
    530                 535                 540

Gly Lys Pro Ala Cys Thr Thr Leu Leu Asn Cys Ala Asn Phe Leu Ser
545                 550                 555                 560

Cys Leu Cys Ser Thr Cys Ala Leu Cys Arg Lys Arg
                565                 570
```

<210> SEQ ID NO 28
<211> LENGTH: 558
<212> TYPE: PRT
<213> ORGANISM: Artificial Sequence
<220> FEATURE:

-continued

<223> OTHER INFORMATION: Influenza virus HA ectodomain fused to T4 foldon multimerizing sequence

<400> SEQUENCE: 28

```
Met Lys Ala Ile Leu Val Val Leu Leu Tyr Thr Phe Ala Thr Ala Asn
1               5                   10                  15

Ala Asp Thr Leu Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Lys His Asn Gly Lys Leu Cys Lys Leu Arg Gly Val
    50                  55                  60

Ala Pro Leu His Leu Gly Lys Cys Asn Ile Ala Gly Trp Ile Leu Gly
65                  70                  75                  80

Asn Pro Glu Cys Glu Ser Leu Ser Thr Ala Ser Ser Trp Ser Tyr Ile
                85                  90                  95

Val Glu Thr Pro Ser Ser Asp Asn Gly Thr Cys Tyr Pro Gly Asp Phe
            100                 105                 110

Ile Asp Tyr Glu Glu Leu Arg Glu Gln Leu Ser Ser Val Ser Ser Phe
        115                 120                 125

Glu Arg Phe Glu Ile Phe Pro Lys Thr Ser Ser Trp Pro Asn His Asp
    130                 135                 140

Ser Asn Lys Gly Val Thr Ala Ala Cys Pro His Ala Gly Ala Lys Ser
145                 150                 155                 160

Phe Tyr Lys Asn Leu Ile Trp Leu Val Lys Lys Gly Asn Ser Tyr Pro
                165                 170                 175

Lys Leu Ser Lys Ser Tyr Ile Asn Asp Lys Gly Lys Glu Val Leu Val
            180                 185                 190

Leu Trp Gly Ile His His Pro Ser Thr Ser Ala Asp Gln Gln Ser Leu
        195                 200                 205

Tyr Gln Asn Ala Asp Thr Tyr Val Phe Val Gly Ser Ser Arg Tyr Ser
    210                 215                 220

Lys Lys Phe Lys Pro Glu Ile Ala Ile Arg Pro Lys Val Arg Asp Gln
225                 230                 235                 240

Glu Gly Arg Met Asn Tyr Tyr Trp Thr Leu Val Glu Pro Gly Asp Lys
                245                 250                 255

Ile Thr Phe Glu Ala Thr Gly Asn Leu Val Val Pro Arg Tyr Ala Phe
            260                 265                 270

Ala Met Glu Arg Asn Ala Gly Ser Gly Ile Ile Ile Ser Asp Thr Pro
        275                 280                 285

Val His Asp Cys Asn Thr Thr Cys Gln Thr Pro Lys Gly Ala Ile Asn
    290                 295                 300

Thr Ser Leu Pro Phe Gln Asn Ile His Pro Ile Thr Ile Gly Lys Cys
305                 310                 315                 320

Pro Lys Tyr Val Lys Ser Thr Lys Leu Arg Leu Ala Thr Gly Leu Arg
                325                 330                 335

Asn Ile Pro Ser Ile Gln Ser Arg Gly Leu Phe Gly Ala Ile Ala Gly
            340                 345                 350

Phe Ile Glu Gly Gly Trp Thr Gly Met Val Asp Gly Trp Tyr Gly Tyr
        355                 360                 365

His His Gln Asn Glu Gln Gly Ser Gly Tyr Ala Ala Asp Leu Lys Ser
    370                 375                 380

Thr Gln Asn Ala Ile Asp Glu Ile Thr Asn Lys Val Asn Ser Val Ile
385                 390                 395                 400
```

-continued

```
Glu Lys Met Asn Thr Gln Phe Thr Ala Val Gly Lys Glu Phe Asn His
                405                 410                 415

Leu Glu Lys Arg Ile Glu Asn Leu Asn Lys Lys Val Asp Asp Gly Phe
            420                 425                 430

Leu Asp Ile Trp Thr Tyr Asn Ala Glu Leu Leu Val Leu Leu Glu Asn
        435                 440                 445

Glu Arg Thr Leu Asp Tyr His Asp Ser Asn Val Lys Asn Leu Tyr Glu
    450                 455                 460

Lys Val Arg Ser Gln Leu Lys Asn Asn Ala Lys Glu Ile Gly Asn Gly
465                 470                 475                 480

Cys Phe Glu Phe Tyr His Lys Cys Asp Asn Thr Cys Met Glu Ser Val
                485                 490                 495

Lys Asn Gly Thr Tyr Asp Tyr Pro Lys Tyr Ser Glu Glu Ala Lys Leu
            500                 505                 510

Asn Arg Glu Glu Ile Asp Gly Val Lys Leu Glu Ser Thr Arg Ile Tyr
        515                 520                 525

Gln Gly Ser Gly Tyr Ile Pro Glu Ala Pro Arg Asp Gly Gln Ala Tyr
    530                 535                 540

Val Arg Lys Asp Gly Glu Trp Val Leu Leu Ser Thr Phe Leu
545                 550                 555


<210> SEQ ID NO 29
<211> LENGTH: 24
<212> TYPE: PRT
<213> ORGANISM: Artificial Sequence
<220> FEATURE:
<223> OTHER INFORMATION: Consensus sequence for a LRR module from
      Lamprey VLR-B antibody
<220> FEATURE:
<221> NAME/KEY: misc_feature
<222> LOCATION: (2)..(24)
<223> OTHER INFORMATION: X" is any amino acid

<400> SEQUENCE: 29

Leu Xaa Xaa Leu Xaa Xaa Leu Xaa Leu Xaa Xaa Asn Xaa Leu Xaa Xaa
1               5                   10                  15

Xaa Pro Xaa Gly Xaa Phe Asp Xaa
            20
```

MULTIMERIZATION OF RECOMBINANT PROTEIN BY FUSION TO A SEQUENCE FROM LAMPREY

This application is a Continuation of U.S. patent application Ser. No. 15/536,726, which was filed on Jun. 16, 2017, which is a 371 application of International Application No. PCT/EP2015/080653, which was filed on Dec. 18, 2015, and claims priority to European Patent Application No. EP 14307096.9, which was filed on Dec. 19, 2014, all of which are incorporated by reference in their entirety.

FIELD OF THE INVENTION

This invention relates generally to the production of multimeric recombinant proteins.

BACKGROUND OF THE INVENTION

Proteins are responsible for a majority of the cellular functions such as molecular recognition (for example in the immune system), signaling pathways (hormones), the transport of metabolites and nutrients and the catalysis of biochemical reactions (enzymes).

The function of proteins results from their three-dimensional structure, that is to say how the amino acids of the polypeptide chain are arranged relative to each other in space. It is usually only in its folded state (native state) that a protein can exert its biological activity.

Whereas most proteins have a primary structure (amino acid sequence), a secondary structure (alpha-helices and beta-sheets), and a tertiary structure (three-dimensional), protein oligomers have an additional level called the quaternary structure that is part of the three-dimensional structure. Oligomers are complexes of several polypeptides. They can contain several copies of an identical protein referred to as a sub-unit and are referred to as homo-oligomers, or they may consist of more than one type of protein sub-unit, in which case they are referred to as hetero-oligomers. Hemoglobin, the oxygen carrier in blood, is an example of a protein containing identical subunits. Nitrogenase, the microbial enzyme responsible for the reduction of nitrogen gas to ammonia, is an example of a protein containing non-identical sub-units.

Numerous recombinant proteins of interest are oligomeric in nature, for example antibodies, many transmembrane proteins such as transmembrane receptors, porins, viral surface antigens, heat shock proteins, viral capsid proteins, ferritin, insulin, many enzymes such as glutathione peroxidase, catalase or superoxide dismutase, collagen and many others.

For instance, influenza virus haemagglutinin (HA) is a homotrimeric glycoprotein on the surface of the virus which is responsible for interaction of the virus with host cell receptors. The three-dimensional structure of HA is described in detail in Nature, 289, 366-373 (1981). Protective immune responses induced by vaccination against influenza virus are primarily directed to the viral HA protein. Recombinant HA protein (rHA) represents therefore an interesting antigen for the development of influenza vaccines.

Another oligomeric antigen of interest is the Invasion Plasmid Antigen D (IpaD) protein of *Shigella* that was found to form either pentamers, or in the presence of IpaB, tetramers, at the needle tip of the bacteria (Cheung et al., Molecular Microbiology, 95(1), 31-50 (2015)).

A further oligomeric antigen of interest is the Membrane expression of Ipa H (MxiH) protein of *Shigella* that was found to form a helical assembly of subunits that produces the *Shigella* needle (Cordes et al., The Journal of Biological Chemistry, 278(19), 17103-17107 (2003)).

One of the challenges in the recombinant protein field is that recombinant proteins do not always have the same three-dimensional conformation as the native protein. Yet the function of proteins often results from their three-dimensional structure.

Similarly, in respect of oligomers, if the recombinant protein does not keep the quaternary structure of the native protein, the function of the recombinant protein may be altered or suppressed.

For instance, William C. Weldon et al., in Plos One, 5(9), e12466 (2010), showed that poor trimerization of a recombinant influenza haemagglutinin could play a role in its low immunogenicity.

There is therefore a need to produce recombinant proteins which better retain the oligomeric structure and desired biological function of the native protein.

Chih-Jen Wei et al., in Journal of Virology, 82(13), 6200-6208 (2008), describe the trimerization of influenza rHA using the foldon sequence of the T4 phage.

SUMMARY OF THE INVENTION

The inventors have surprisingly determined that a fragment of the sequence of the lamprey variable lymphocyte receptor B (VLR-B) antibody may be used to multimerize a heterologous fusion protein.

Lamprey is a jawless vertebrate with an adaptive immune system comprised of clonally diverse lymphocytes that express variable lymphocyte receptors (VLRs) created by combinatorial assembly of leucine-rich repeat gene segments. The VLR-B can be secreted and can function analogously to antibodies in jawed vertebrates.

Surprisingly we found that fusion of a nucleic acid sequence encoding a protein of interest and a nucleic acid sequence encoding a peptide found at the extreme C-terminus of lamprey VLR-B antibodies, i.e. C-terminal to the Stalk region (the domain named "C-TERM" in FIG. 11C of WO 2008/016,854), encodes a recombinant protein which is capable of oligomerization with several degrees of oligomerization.

More surprisingly we found that the multimeric recombinant proteins obtained are stable.

And even more surprisingly we found that the stable multimeric recombinant proteins obtained have several degrees of oligomerization while retaining the biological activity of their native form.

According to an embodiment, a molecule is obtained which comprises a first amino acid sequence which has at least 80% identity to SEQ ID NO: 1 and a second amino acid sequence which is heterologous to said first sequence.

According to another embodiment, a recombinant protein is obtained which comprises a first amino acid sequence which has at least 80% identity to SEQ ID NO: 1 and a second amino acid sequence which is heterologous to said first sequence.

According to another embodiment a recombinant nucleic acid is constructed which comprises a first nucleic acid sequence with at least 80% identity to SEQ ID NO: 3 and a second nucleic acid sequence which is heterologous to said first sequence.

Another aspect is directed to an expression cassette comprising a recombinant nucleic acid as described above wherein the recombinant nucleic acid is operably linked to a promoter.

Another aspect is directed to a host cell transformed with the expression cassette.

The invention is also directed to a stable homo-multimeric recombinant protein which comprises a protein selected from the group consisting of the ectodomain of an influenza HA protein, a *Shigella* IpaD protein and a *Shigella* MxiH protein, which is fused to a protein having an amino acid sequence with at least 80% identity to SEQ ID NO: 1.

Another embodiment is directed to a pharmaceutical composition comprising a molecule or a recombinant protein of the invention and a pharmaceutically acceptable carrier or diluent.

In another aspect the invention provides an immunogenic composition comprising a molecule or a recombinant protein of the invention.

In another embodiment, the molecule or the recombinant protein of the invention is for use as a medicament.

In a further aspect of the invention, the molecule or the recombinant protein of the invention is for use in inducing an immune response to an antigen in a subject.

The invention is also directed to a method for multimerizing a recombinant protein comprising:

a) fusing a nucleic acid sequence having at least 80% identity to SEQ ID NO: 3 to the nucleic acid sequence coding for said recombinant protein, with the proviso that said recombinant protein is not a lamprey VLR-B antibody protein,
b) expressing the fusion protein encoded by said nucleic acid sequence, under conditions which lead to the multimerization of said recombinant protein.

Definitions

In the context of the invention, protein "oligomers" or "polymers" or "multimers" have the same meaning, i.e. proteins having a quaternary structure, being complexes of at least two polypeptides, said polypeptides may be identical or different. Accordingly, in the context of the invention, "multimerization", "oligomerization" and "polymerization" have the same meaning, as do "multimerized", "oligomerized" and "polymerized" or "multimerizing", "oligomerizing" and "polymerizing".

"Recombinant proteins" are proteins encoded by recombinant nucleic acids. They are expressed from recombinant nucleic acids in a host cell. "Recombinant nucleic acid" is used herein to describe a nucleic acid molecule which, by virtue of its origin or manipulation is not associated with all or a portion of the polynucleotide with which it is associated in nature and/or is linked to a polynucleotide other than that to which it is linked in nature. The recombinant proteins of the invention comprise a protein fragment from the VLR-B antibody of lamprey and a protein of interest which is heterologous to the protein fragment from the VLR-B antibody of lamprey. As described herein, the recombinant proteins of the invention comprise a protein fragment from the extreme C-terminus of VLR-B antibodies of Lamprey.

In the context of the invention, a "molecule" is the junction by any means between a protein fragment from the VLR-B antibody of lamprey and a protein of interest which is heterologous to the protein fragment from the VLR-B antibody of lamprey. For example, a molecule of the present invention may be created by joining the VLR-B protein and the heterologous protein of interest via a covalent linkage. Examples of such covalent linkages include a peptide bond, an ester linkage, an amide linkage and a disulfide bond. As described herein, the protein fragment from the VLR-B antibody of lamprey comes from the extreme C-terminus of VLR-B antibodies of Lamprey.

By "first amino acid sequence" and "second amino acid sequence" in the description of the molecule or the recombinant protein of the invention, it is not meant that a specific order of the sequences is contemplated. It is just for clarity of the embodiment to better distinguish the two sequences comprised in the molecule or recombinant protein of the invention.

By "first nucleic acid sequence" and "second nucleic acid sequence" in the description of the recombinant nucleic acid of the invention, it is not meant that a specific order of the sequences is contemplated. It is just for clarity of the embodiment to better distinguish the two sequences comprised in the recombinant nucleic acid of the invention.

In the context of the invention, the first sequence, either amino acid or nucleic acid sequence, designates respectively, an amino acid or a nucleic acid sequence, derived from the C-terminus of the VLR-B antibody of lamprey. According to the invention, the size of the first polypeptide sequence is typically between 24 and 43 amino acids long, particularly between 30 and 43 amino acids long, the bounds being included. Accordingly the size of the first polypeptide sequence may preferably be about 30, 31, 32, 33, 34, 35, 36, 37, 38, 39, 40, 41, 42 or 43 amino acids long. According to the invention, the size of the first nucleic acid sequence is typically between 72 and 129 base pairs long, particularly between 90 and 129 base pairs long, the bounds being included. Accordingly the size of the first nucleic acid sequence may preferably be about 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128 or 129 base pairs long.

In the context of the invention, the second sequence, either amino acid or nucleic acid sequence, designates respectively the amino acid sequence of a protein of interest or a fragment thereof or the nucleic acid sequence encoding a protein of interest or a fragment thereof. In the context of the present invention, a "fragment" of a protein as referred to herein retains the biological function of the full-length protein from which it is derived. Thus a fragment according to the present invention may be at least 20, at least 50, at least 75, at least 100 or at least 150 amino acids long.

Two sequences which are contained within a single recombinant molecule are "heterologous" relative to each other when they are not normally associated with each other in nature. In the context of the invention, a second sequence that is heterologous to a first sequence, either amino acid or nucleic acid sequence, means that the second heterologous sequence is not or does not comprise a sequence from the VLR-B antibody of lamprey. In the context of the invention, the heterologous sequence is not an amino acid sequence of, or a nucleic acid sequence coding for a polyhistidine-tag (His-tag). Furthermore, it is preferred that the heterologous sequence according to the present invention is at least 5, at least 10 or at least 15 amino acids long (or is a nucleotide sequence encoding such an amino acid sequence).

"Fusion proteins" are proteins created through the joining of two or more genes that originally coded for separate proteins. This typically involves removing the stop codon from a DNA sequence coding for the first protein, then appending the DNA sequence of the second protein in frame through ligation or overlap extension PCR. If more than two genes are fused, the other genes are added in frame in the same manner. The resulting DNA sequence will then be expressed by a cell as a single protein. The fusion proteins of the invention are obtained from a nucleic acid coding for a protein fragment from the VLR-B antibody of lamprey fused to a nucleic acid coding for any or all of proteins of interest or fragments thereof. In the context of the invention, the protein can be engineered to include the full sequence of a protein of interest, or only a portion of a protein of interest. The joining of the two or more genes may be made in any order, i.e. the sequences coding for proteins of interest, or fragments thereof, are located either 3' or 5' from the sequence coding for a fragment of the lamprey VLR-B antibodies. Preferably, the sequences coding for the proteins of interest, or fragments thereof, are located 5' from the sequence coding for a fragment of the lamprey VLR-B antibodies. As described elsewhere herein, in the context of the present invention, the protein fragment from the VLR-B antibody of lamprey comes from the extreme C-terminus of the lamprey VLR-B antibody.

As used herein, a first sequence having at least x% identity to a second sequence means that x% represents the number of amino acids in the first sequence which are identical to their matched amino acids of the second sequence when both sequences are optimally aligned via a global alignment, relative to the total length of the second amino acid sequence. Both sequences are optimally aligned when x is maximum. The alignment and the determination of the percentage of identity may be carried out manually or automatically using a global alignment algorithm, for instance the Needleman and Wunsch algorithm, described in Needleman and Wunsch, J. Mol Biol., 48, 443-453 (1970), with for example the following parameters for polypeptide sequence comparison: comparison matrix: BLOSUM62 from Henikoff and Henikoff, Proc. Natl. Acad. Sci. USA., 89, 10915-10919 (1992), gap penalty: 8 and gap length penalty: 2; and the following parameters for polynucleotide sequence comparison: comparison matrix: matches=+10, mismatch=0; gap penalty: 50 and gap length penalty: 3.

A program which may be used with the above parameters is publicly available as the "gap" program from Genetics Computer Group, Madison Wis. The aforementioned parameters are the default parameters respectively for peptide comparisons (along with no penalty for end gaps) and for nucleic acid comparisons.

An "antigen" refers to any agent, preferably a macromolecule, which can elicit an immunological response in an individual. The term may be used to refer to an individual macromolecule or to a homogeneous or heterogeneous population of antigenic macromolecules. As used herein, "antigen" is preferably used to refer to a protein molecule or portion thereof which contains one or more epitopes. An epitope is the part of the antigen that is recognized by antibodies or T cell receptors. Some epitopes are referred to as discontinuous conformational epitope. This means that the amino acids comprising these epitopes are proximal to each other in the three-dimensional structure of the protein, but appear distant from each other when one looks strictly at the one-dimensional linear amino acid sequence. Consequently, it is clear that the three-dimensional structure of the protein is extremely important in terms of what the immune system actually sees.

The "ectodomain" is the portion of a transmembrane anchored protein that extends beyond the membrane into the extracellular space.

"Scaffolds" are specific ligand-binding artificial structures usually generated from a combinatorial library of a chosen protein scaffold, by selective random mutagenesis of appropriate exposed surface residues followed by selection of variants with the desired binding activity. Kaspar Binz et al. reviewed numerous alternative protein scaffolds, in Nature Biotechnology, 86 (10), 1257-1268 (2005), and the well-established techniques to design the combinatorial library from them and to select the relevant variant, most predominantly phage display and related methods.

BRIEF DESCRIPTION OF THE DRAWINGS

Various features of the embodiments can be more fully appreciated, with reference to the following detailed description of the embodiments and accompanying figures, in which.

(a) pLexsy-I-bleo2 expression cassette.

(b) Seq1 corresponds to SEQ ID NO: 7 and is the nucleic acid sequence, coding for the first tested sequence, fused to the nucleic acid sequence coding for the ectodomain of the HA protein of the influenza A/California/07/2009 (H1N1).

(c) Seq2 corresponds to SEQ ID NO: 8 and is the nucleic acid sequence, coding for the second tested sequence, fused to the nucleic acid sequence coding for the ectodomain of the HA protein of the influenza A/California/07/2009 (H1N1).

(d) Seq3 corresponds to SEQ ID NO: 9 and is the nucleic acid sequence, coding for the third tested sequence, fused to the nucleic acid sequence coding for the ectodomain of the HA protein of the influenza A/California/07/2009 (H1N1).

Figure 2:
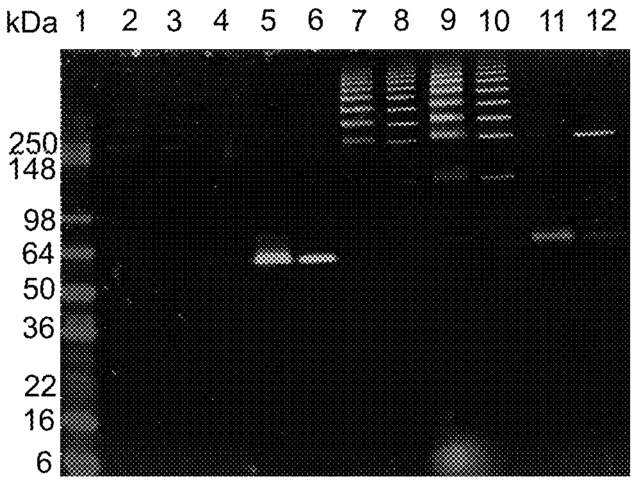

FIG. 2 shows the Western Blot of a SDS PAGE gel of different recombinant HA ectodomain proteins.

Lane 1: molecular weight size marker

Lane 2: negative control—no induction of the promoter, with heat treatment

Lane 3: negative control—no induction of the promoter

Lane 4: negative control—non relevant antigen (flu antibody), with heat treatment Lane 5: positive control—rHA ectodomain with no polymerizing sequence, with heat treatment Lane 6: positive control—rHA ectodomain with no polymerizing sequence Lane 7: rHA ectodomain fused to the polymerizing sequence SEQ ID NO: 1, according to an embodiment, with heat treatment Lane 8: rHA ectodomain fused to the polymerizing sequence SEQ ID NO: 1, according to an embodiment Lane 9: rHA ectodomain fused to the polymerizing sequence SEQ ID NO: 2, according to an embodiment, with heat treatment Lane 10: rHA ectodomain fused to the polymerizing sequence SEQ ID NO: 2, according to an embodiment Lane 11: rHA ectodomain fused to the polymerizing sequence SEQ ID NO: 5, with heat treatment Lane 12: rHA ectodomain fused to the polymerizing sequence SEQ ID NO: 5

Figure 3:
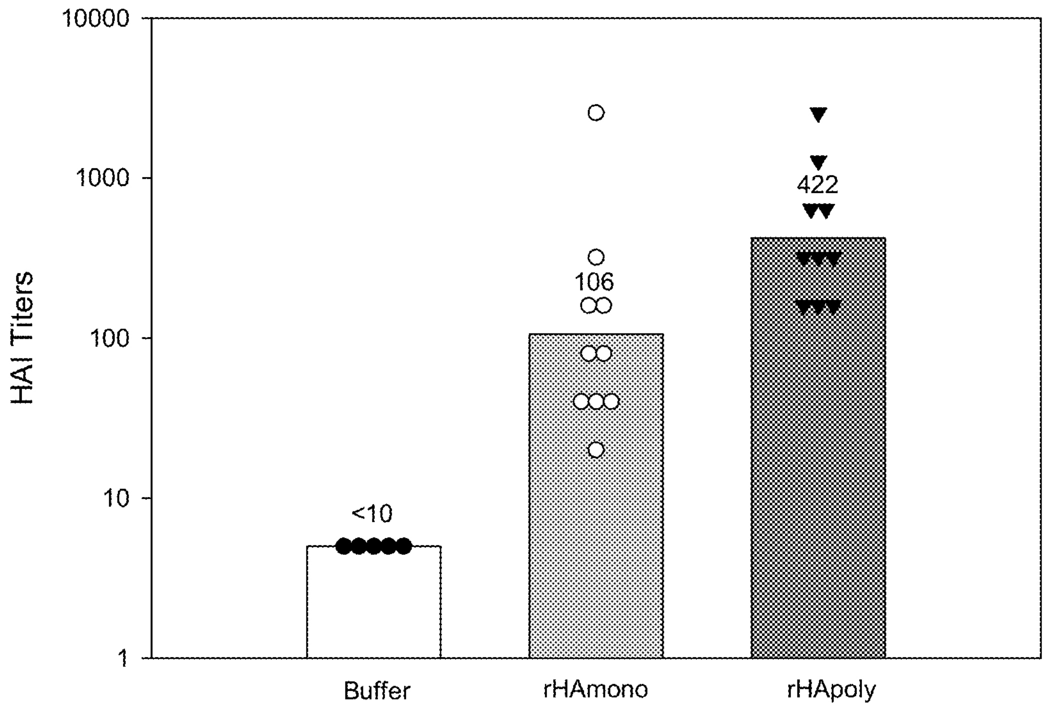

FIG. 3 shows the inhibition of haemagglutination mean antibody titers in mice immunized with the multimeric rHA according to an embodiment.

Figure 4:
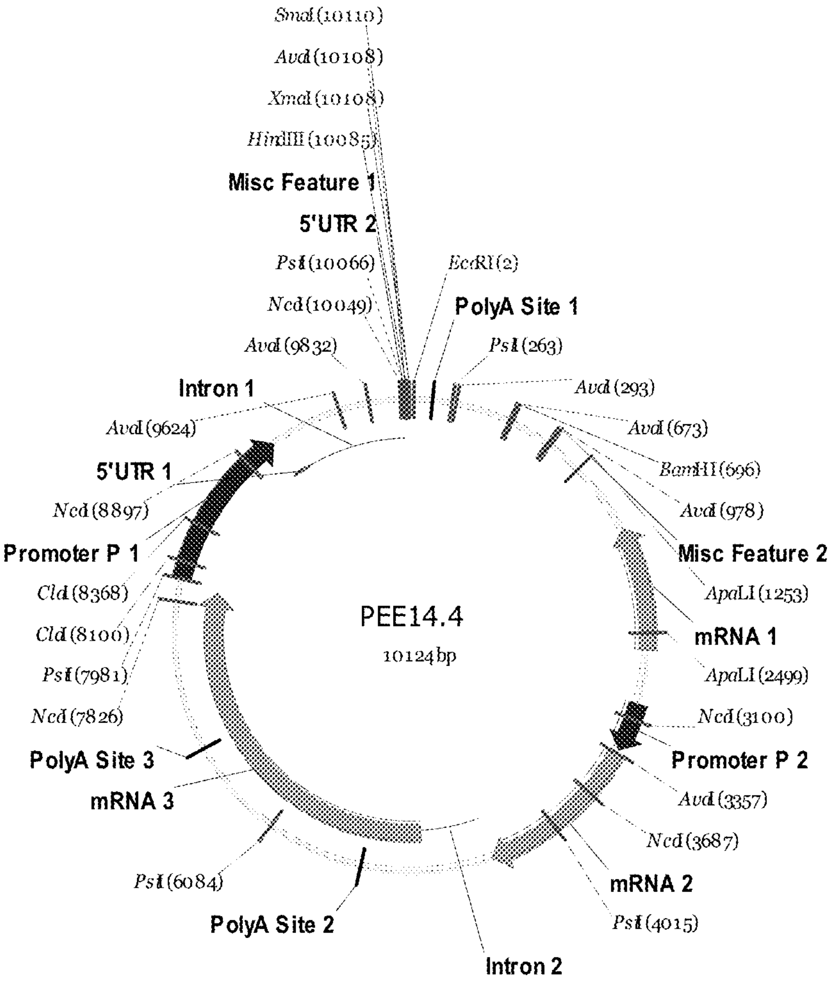

FIG. 4 shows the pEE14.4 expression cassette used to produce recombinant influenza HA ectodomain proteins in CHO cells.

Figure 5:
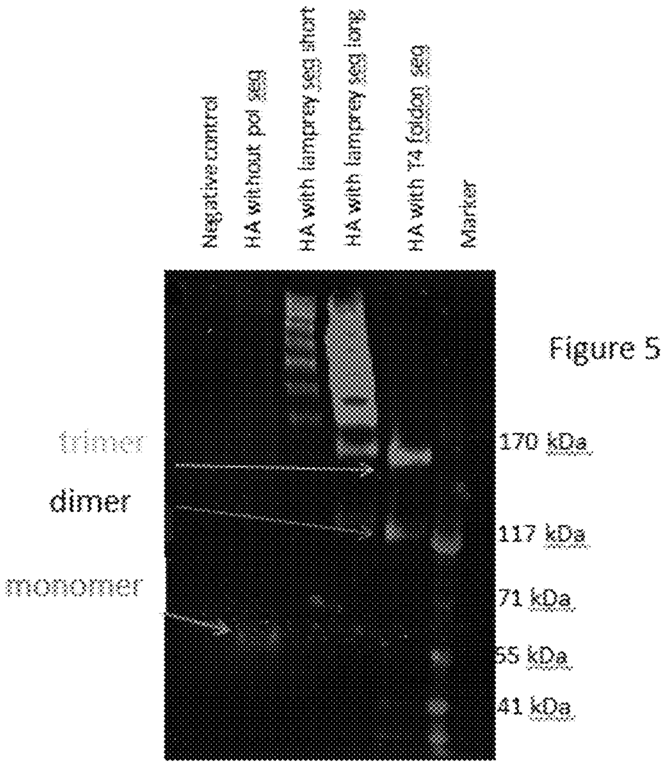

FIG. 5 shows the Western Blot of a SDS PAGE gel of different recombinant HA ectodomain proteins expressed in CHO cells.

Figure 6:
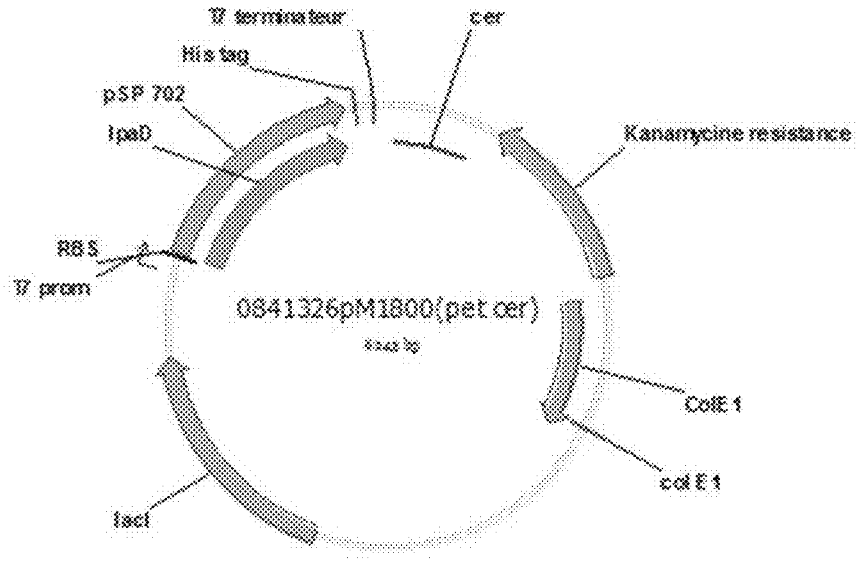

FIG. 6 shows the pM1800 expression cassette used to produce recombinant *Shigella flexneri* IpaD proteins in *E. coli*.

Figure 7:
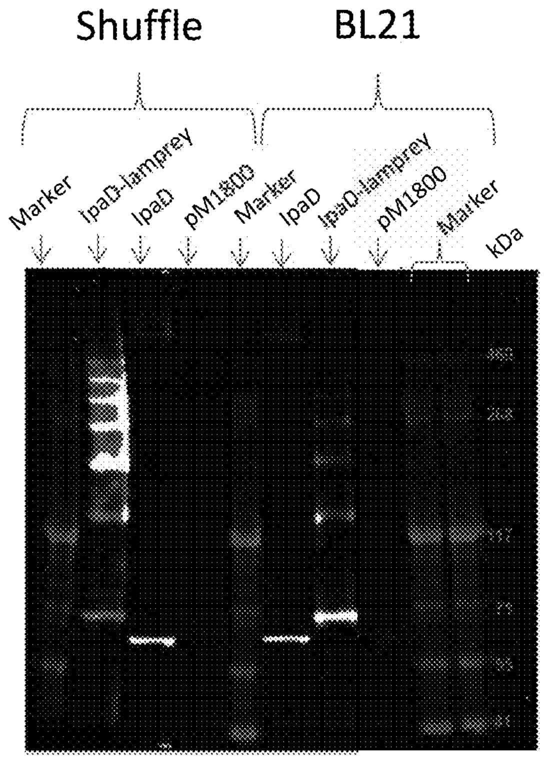

FIG. 7 shows the Western Blot of a SDS PAGE gel of different recombinant *Shigella flexneri* IpaD proteins.

Figure 8:

FIG. 8 shows the Western Blot of a SDS PAGE gel of different recombinant *Shigella flexneri* IpaD proteins with His-tag.

FIG. 9 shows the Western Blot of a SDS PAGE gel of different heat-treated recombinant *Shigella flexneri* IpaD proteins.

FIG. 10 shows the Western Blot of a SDS PAGE gel of different recombinant *Shigella flexneri* MxiH proteins. "IS" means insoluble (pellet sample) while "S" means soluble (supernatant sample).

Figure 11:
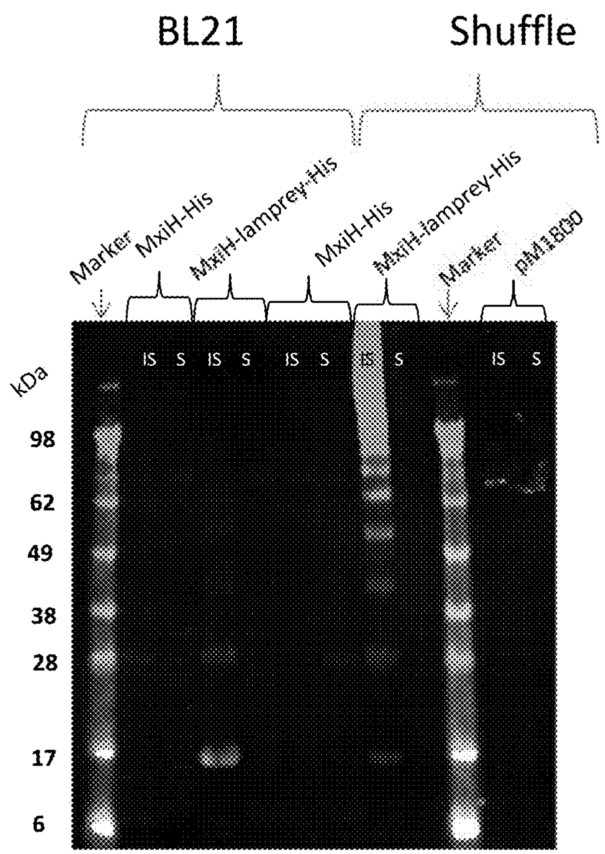

FIG. 11 shows the Western Blot of a SDS PAGE gel of different recombinant *Shigella flexneri* MxiH proteins with His-tag. "IS" means insoluble (pellet sample) while "S" means soluble (supernatant sample)

DESCRIPTION OF THE EMBODIMENTS

According to an embodiment, a molecule is obtained which comprises a first amino acid sequence which has at least 80% identity to SEQ ID NO: 1 and a second amino acid sequence which is heterologous to said first sequence. In particular, the molecule according to the invention comprises a first amino acid sequence which has at least 85% identity, at least 90% identity, at least 95% identity, at least 97% identity, at least 98% identity, at least 99% identity or even 100% identity to SEQ ID NO: 1.

According to an embodiment, a molecule is obtained which comprises a first amino acid sequence which has at least 80% identity to SEQ ID NO: 2 and a second amino acid sequence which is heterologous to said first sequence. In particular, the molecule according to the invention comprises a first amino acid sequence which has at least 85% identity, at least 90% identity, at least 95% identity, at least 97% identity, at least 98% identity, at least 99% identity or even 100% identity to SEQ ID NO: 2.

In a preferred embodiment the 7 cysteines that correspond to positions 2, 7, 13, 19, 21, 24 and 27 of SEQ ID NO: 1 are conserved in the first io amino acid sequence. The molecule of the invention does not comprise a lamprey VLR-B antibody protein.

In a preferred embodiment the 8 cysteines that correspond to positions 2, 15, 20, 26, 32, 34, 37 and 40 of SEQ ID NO: 2 are conserved in the first amino acid sequence. The molecule of the invention does not comprise a lamprey VLR-B antibody protein.

According to an embodiment, a recombinant protein is obtained which comprises a first amino acid sequence which has at least 80% identity to SEQ ID NO: 1 and a second amino acid sequence which is heterologous to said first sequence. In particular, the recombinant protein according to the invention comprises a first amino acid sequence which has at least 85% identity, at least 90% identity, at least 95% identity, at least 97% identity, at least 98% identity, at least 99% identity or even 100% identity to SEQ ID NO: 1.

According to an embodiment, a recombinant protein is obtained which comprises a first amino acid sequence which has at least 80% identity to SEQ ID NO: 2 and a second amino acid sequence which is heterologous to said first sequence. In particular, the molecule according to the invention comprises a first amino acid sequence which has at least 85% identity, at least 90% identity, at least 95% identity, at least 97% identity, at least 98% identity, at least 99% identity or even 100% identity to SEQ ID NO: 2.

In a preferred embodiment the 7 cysteines that correspond to positions 2, 7, 13, 19, 21, 24 and 27 of SEQ ID NO: 1 are conserved in the first amino acid sequence. The recombinant protein of the invention does not comprise a lamprey VLR-B antibody protein.

Preferably, a molecule or recombinant protein of the invention does not comprise a leucine-rich repeat (LRR) module from a lamprey VLR-B antibody. A consensus sequence for an LRR module from a lamprey VLR-B antibody is LXXLXXLXLXXNXLXXXPXGXFDX, where X may be any amino acid (SEQ ID NO: 29). Preferably, a molecule or recombinant protein of the invention does not comprise a sequence falling within the scope of the group of sequences defined by SEQ ID NO: 29, i.e. a molecule or recombinant protein of the invention does not comprise SEQ ID NO: 29. Specific examples of LRR modules (see FIG. 11C of WO 2008/016854) include an N-terminal cap LRR (referred to as LRRNT), LRR1, variable LRR modules (referred to as LRRV), an end LRRV (known as LRRVe) and a C-terminal cap LRR (referred to as LRRCT). Preferably, a molecule or recombinant protein of the invention does not comprise one or more of an LRRNT, an LRR1, an LRRV and an LRRCT module from a lamprey VLR-B antibody. Lamprey VLR-B antibodies also comprise a connecting peptide (CP) and a Stalk region in addition to the LRR modules. Preferably, a molecule or recombinant protein of the invention does not comprise a CP or a Stalk region from a lamprey VLR-B antibody. Preferably, a molecule or recombinant protein of the invention does not comprise an LRR module, a CP or a Stalk region from a lamprey VLR-B antibody. Preferably, the only lamprey-derived amino acid sequence in a molecule or recombinant protein of the present invention is derived from the extreme C-terminus of a lamprey VLR-B antibody (i.e. the section of the protein C-terminal to the Stalk region, see FIG. 11C of WO 2008/016854). Preferably, the only lamprey-derived amino acid sequence in a molecule or recombinant protein of the present invention is a sequence having at least 80% identity to SEQ ID NO: 1 or io SEQ ID NO: 2, for example at least 85% identity, at least 90% identity, at least 95% identity, at least 97% identity, at least 98% identity, at least 99% identity or even 100% identity to SEQ ID NO: 1 or SEQ ID NO: 2.

Another embodiment is directed to a recombinant nucleic acid which comprises a first nucleic acid sequence with at least 80% identity to SEQ ID NO: 3 and a second nucleic acid sequence which is heterologous to said first sequence. In particular, the recombinant nucleic acid according to the invention comprises a first nucleic acid sequence which has at least 85% identity, at least 90% identity, at least 95% identity, at least 97% identity, at least 98% identity, at least 99% identity or even 100% identity to SEQ ID NO: 3.

Another embodiment is directed to a recombinant nucleic acid which comprises a first nucleic acid sequence with at least 80% identity to SEQ ID NO: 4 and a second nucleic acid sequence which is heterologous to said first sequence. In particular, the recombinant nucleic acid according to the invention comprises a first nucleic acid sequence which has at least 85% identity, at least 90% identity, at least 95% identity, at least 97% identity, at least 98% identity, at least 99% identity or even 100% identity to SEQ ID NO: 4.

In a preferred embodiment the first nucleic acid sequence encodes an amino acid sequence which comprises cysteine residues at positions within said amino acid sequence that correspond to positions 2, 7, 13, 19, 21, 24 and 27 of SEQ ID NO:1. The recombinant nucleic acid of the invention does not encode a lamprey VLR-B antibody. In a preferred embodiment the first nucleic acid sequence encodes an amino acid sequence which comprises cysteine residues at positions within said amino acid sequence that correspond to positions 2, 15, 20, 26, 32, 34, 37 and 40 of SEQ ID NO: 2.

Preferably, a recombinant nucleic acid of the invention does not encode a leucine-rich repeat (LRR) module from a lamprey VLR-B antibody. In particular, a recombinant nucleic acid as described herein does not encode an amino acid sequence having the sequence of SEQ ID NO: 29. Preferably, a recombinant nucleic acid of the invention does not encode one or more of an LRRNT module, an LRR1 module, an LRRV module, an LRRCT module, a CP and a Stalk region from a lamprey VLR-B antibody. Preferably, the only lamprey-derived amino acid sequence which is encoded by a recombinant nucleic acid of the present invention is derived from the extreme C-terminus of a lamprey VLR-B antibody (i.e. the section of the protein C-terminal to the Stalk region, see FIG. 11C of WO 2008/016854). Preferably, the only lamprey-derived nucleic acid sequence in a recombinant nucleic acid of the present invention is a sequence having at least 80% identity to SEQ ID NO: 3 or SEQ ID NO: 4, for example at least 85% identity, at least 90% identity, at least 95% identity, at least 97% identity, at least 98% identity, at least 99% identity or even 100% identity to SEQ ID NO: 3 or SEQ ID NO: 4.

A linker may be inserted between the first amino acid sequence and the second heterologous amino acid sequence. Linkers may be a short peptide sequence or another suitable covalent link between protein domains. Preferably, the linker is a short peptide sequence. Preferably said peptide linkers are composed of flexible residues like glycine (G) and serine (S) so that the adjacent protein domains are free to move relative to one another. Preferably said linker is at least 3, 4, 5, 6, 7, 8, 9, 10, 11, 12, 13, 14 or at least 15 amino acid residues long. Any possible linker known by the person skilled in the art may be used for the purpose of the invention. For instance the linker may be G6S9 (which means 6 glycines followed by 9 serines) as used by William C. Weldon et al., in Plos One, 5(9), e12466 (2010); G8 as used by Ludmilla Sissoëff et al., in Journal of General Virology, 86, 2543-2552 (2005), or G4S3.

A spacer nucleic acid sequence coding for a peptide linker as described above may be inserted between the first nucleic acid sequence and the second heterologous nucleic acid sequence.

In a preferred embodiment the heterologous protein of interest is an antigen or fragment thereof. In this embodiment, the heterologous amino acid sequence is from an antigen amino acid sequence or the heterologous nucleic acid sequence is from an antigen nucleic acid sequence. For the purpose of the present invention, antigens can be obtained or derived from any appropriate source. Preferably, the source of the antigen is selected from the group consisting of influenza virus, HIV, cytomegalovirus, dengue virus, yellow fever virus, tick-borne encephalitis virus, hepatitis virus, japanese encephalitis virus, human papillomavirus, coxsackievirus, herpes simplex virus, rubella virus, mumps virus, measles virus, rabies virus, polio virus, rotavirus, respiratory syncytial virus, Ebola virus, Chikungunya virus, *Mycobacterium tuberculosis, Staphylococcus aureus, Staphylococcus epidermidis, E. coli, Clostridium difficile, Bordetella pertussis, Clostridium tetani, Haemophilus influenzae* type b, *Chlamydia pneumoniae, Chlamydia trachomatis, Porphyromonas gingivalis, Pseudomonas aeruginosa, Mycobacterium diphtheriae, Shigella, Neisseria meningitidis, Streptococcus pneumoniae* and *Plasmodium falciparum*. Preferably, the antigen has a molecular weight of less than 150 kDa, less than 125 kDa or less than 100 kDa. Most preferably, the antigen has a molecular weight of less than 100 kDa.

Preferably, the source of the antigen is selected from the group consisting of influenza virus, cytomegalovirus, dengue virus, yellow fever virus, hepatitis virus, japanese encephalitis virus, human papillomavirus, herpes simplex virus, rabies virus, polio virus, rotavirus, respiratory syncytial virus, Ebola virus, Chikungunya virus, *Mycobacterium tuberculosis, Staphylococcus aureus, Staphylococcus epidermidis, E. coli, Clostridium difficile, Bordetella pertussis, Clostridium tetani, Haemophilus influenzae* type b, *Mycobacterium diphtheriae, Shigella, Neisseria meningitidis* and *Streptococcus pneumoniae*. Preferably, the source of the antigen is selected from influenza virus and *Shigella*.

In some embodiments a molecule or a recombinant protein of the invention may comprise more than one antigen which is heterologous to the lamprey VLR-B sequence as described herein. When the molecule or the recombinant protein comprises several antigens, these antigens are independently a complete protein of interest or a fragment of a protein of interest, and may be from the same organism or from different organisms. The antigen may be a fusion antigen from different proteins, or fragments thereof, of the same organism or from different organisms.

Preferably, the antigen for use in a molecule or a recombinant protein of the present invention is from an influenza virus. The influenza virus may be a seasonal or a pandemic influenza virus. The influenza virus may be any subtype of A strains, B strains, or C strains. In particular, the influenza A virus is selected from the group consisting of the H1N1, H2N2, H3N1, H3N2, H3N8, H5N1, H7N1, H7N7, H1N2, H9N2, H7N2, H7N3, and H10N7 viruses.

Preferably, the influenza antigen is selected from a haemagglutinin (HA), or fragment thereof, a matrix 2 protein (M2) (Holsinger et al., Virology, 183, 32-43 (1991)), or fragment thereof, and an HAM2 fusion protein. In the HAM2 fusion protein, HA and M2 are independently the complete protein or a fragment of the protein. In a more preferred embodiment, the antigen is an influenza haemagglutinin or fragment thereof.

Furthermore, for the purposes of the present invention, an antigen includes a protein having modifications, such as deletions, additions and substitutions to the native sequence, as long as the protein maintains sufficient immunogenicity. These modifications may be deliberate, for example through site-directed mutagenesis, or may be accidental, such as mutations which occur during expression of the antigens in a host cell. The antigen may also be a protein or a fragment thereof encoded by a consensus sequence.

Preferably, the antigen is the ectodomain of a transmembrane anchored protein. The ectodomain corresponds to the native protein wherein the transmembrane domain and cytoplasmic tail, if any, have been deleted in order to allow its secretion in the host which produces the antigen and its easy downstream purification.

Preferably, the antigen is the ectodomain of influenza virus HA.

In another preferred embodiment the protein of interest (i.e. the antigen for use in an antigen or recombinant protein of the present invention) is selected from cytomegalovirus (CMV) glycoprotein B (gB) (Scheffczick et al., FEBS Letters, 506, 113-116 (2001)), or a fragment thereof, cytomegalovirus UL130 protein (Patrone et al., J. Virol. 79(13), 8361-8373 (2005)) or a fragment thereof, ora gB-UL130 fusion protein, and the HIV glycoprotein 41 (Gp41)

(Pancera et al., Nature, 514(7523), 455-461 (2014)), or a fragment thereof. In the gB-UL130 fusion protein, gB and UL130 are independently the complete protein or a fragment thereof.

In a more preferred embodiment, the antigen is the ectodomain of the CMV gB protein or of the HIV Gp41 protein. In the gB-UL130 fusion protein, gB is the complete protein or the ectodomain of the gB protein. In another preferred embodiment, the antigen is selected from the group consisting of the HIV Gp41 protein and the cytomegalovirus UL130 protein.

In another preferred embodiment, the antigen is a bacterial protein, for example a protein from *Shigella* sp. Preferably the antigen is from *Shigella sonnei* or *Shigella flexneri*. Preferably the antigen is IpaD or MxiH from *Shigella sonnei* or *Shigella flexneri*. In certain embodiments, the antigen is preferably not the CMV gB protein or the ectodomain of the CMV gB protein.

In another preferred embodiment, the protein of interest is an antibody or a scaffold. In this embodiment, the heterologous amino acid sequence is from an antibody or scaffold amino acid sequence or the heterologous nucleic acid sequence is from an antibody or scaffold nucleic acid sequence.

In a preferred embodiment the antibody or scaffold is specific for an antigen, i.e. specifically binds to an antigen. For the purpose of the present invention, antigens for which the antibody or scaffold is specific for can be obtained or derived from any appropriate source. Preferably, the source of the antigen is selected from the group consisting of influenza virus, HIV, cytomegalovirus, dengue virus, yellow fever virus, tick-borne encephalitis virus, hepatitis virus, japanese encephalitis virus, human papillomavirus, coxsackievirus, herpes simplex virus, rubella virus, mumps virus, measles virus, rabies virus, polio virus, rotavirus, respiratory syncytial virus, Ebola virus, Chikungunya virus, *Mycobacterium tuberculosis, Staphylococcus aureus, Staphylococcus epidermidis, E. coli, Clostridium difficile, Bordetella pertussis, Clostridium tetani, Haemophilus influenzae* type b, *Chlamydia pneumoniae, Chlamydia trachomatis, Porphyromonas gingivalis, Pseudomonas aeruginosa, Mycobacterium diphtheriae, Shigella, Neisseria meningitidis, Streptococcus pneumoniae* and *Plasmodium falciparum*.

Preferably, the source of the antigen is selected from the group consisting of influenza virus, cytomegalovirus, dengue virus, yellow fever virus, hepatitis virus, japanese encephalitis virus, human papillomavirus, herpes simplex virus, rabies virus, polio virus, rotavirus, respiratory syncytial virus, Ebola virus, Chikungunya virus, *Mycobacterium tuberculosis, Staphylococcus aureus, Staphylococcus epidermidis, E. coli, Clostridium difficile, Bordetella pertussis, Clostridium tetani, Haemophilus influenzae* type b, *Mycobacterium diphtheriae, Shigella, Neisseria meningitidis* and *Streptococcus pneumoniae*.

In a preferred embodiment the antibody is one of the alternative formats described by Roland Kontermann in Current Opinion in Molecular Therapeutics, 12(2), 176-183 (2010). In particular, the antibody is selected from the group consisting of a monoclonal antibody, a single domain antibody (dAb), a single-chain variable fragment (scFv), a Fab, a F(ab')2 and a diabody (Db). In this embodiment, the heterologous amino acid sequence or the heterologous nucleic acid sequence is respectively from a monoclonal antibody, a dAb, a scFv, a Fab, a F(ab')2 or a Db amino acid sequence, or from a monoclonal antibody, a dAb, a scFv, a Fab, a F(ab')2 or a Db nucleic acid sequence.

Roland Kontermann also described bi-specific antibody formats in Current Opinion in Molecular Therapeutics, 12(2), 176-183 (2010). In some embodiments, the molecule, e.g. a recombinant protein, of the invention is a bi-specific antibody or a bi-specific scaffold, i.e. an antibody or a scaffold specific for two different antigens, or is a multi-specific antibody or a multi-specific scaffold, i.e. an antibody or a scaffold specific for more than two different antigens. In these embodiments, the heterologous amino acid sequence comprises at least two different antibody, monoclonal antibody, dAb, scFv, Fab, F(ab')2, Db or scaffold amino acid sequences, or the heterologous nucleic acid sequence comprises at least two different antibody, monoclonal antibody, dAb, scFv, Fab, F(ab')2, Db or scaffold nucleic acid sequences. The joining of the two or more genes may be made in any order, i.e. the sequences coding for the two or more proteins of interest, or fragments thereof, are located either 3' or 5' of the sequence coding for the fragment of the lamprey VLR-B antibody according to the present invention, or one of the sequences coding for a protein of interest, or fragment thereof, is located 5' of the sequence coding for the fragment of the lamprey VLR-B antibody according to the present invention and the other sequence coding for a protein of interest, or fragment thereof, is located 3'. Preferably, the sequences coding for the two or more proteins of interest, or fragments thereof, are located 5' from the io sequence coding for the fragment of the lamprey VLR-B antibody according to the present invention.

The molecule or the recombinant protein of the invention may be synthesized by any method well-known to the skilled person. Such methods include conventional chemical synthesis, in solid phase (R. B. Merrifield, J. Am. Chem. Soc., 85 (14), 2149-2154 (1963)), or in liquid phase, enzymatic synthesis (K. Morihara, Trends in Biotechnology, 5(6), 164-170 (1987)) from constitutive amino acids or derivatives thereof, cell-free protein synthesis (Katzen et al., Trends in Biotechnology, 23(3), 150-156 (2005)), as well as biological production methods by recombinant technology.

Any method known to the skilled person may be used for the chemical conjugation between the first amino acid sequence and the second amino acid sequence. Such methods include conventional chemical conjugation via a peptide bond (e.g. expression of the first and second amino acid sequences as a fusion protein from a recombinant nucleic acid), optionally with a peptide linker, or conjugation via any covalent link, e.g. a peptide bond, an ester linkage, an amide linkage or a disulfide bond. Preferably the first and second amino acid sequences are expressed together as a fusion protein.

Chemical synthesis of the molecule or recombinant protein of the invention can be particularly advantageous because it allows high purity, the absence of undesired by-products and ease of production.

The molecule or protein of the invention obtained by such methods can then optionally be purified using any method known to the skilled person.

Preferably, the recombinant protein of the invention is obtained using a biological production process with a recombinant host cell. In such a process, an expression cassette, containing a nucleic acid encoding the protein or fusion protein of the invention, is transferred into a host cell, which is cultured in conditions enabling expression of the corresponding protein or fusion protein. The protein or fusion protein thereby produced can then be recovered and purified.

The present invention is also directed to an expression cassette comprising a recombinant nucleic acid of the invention, wherein the recombinant nucleic acid is operably linked to a promoter. A number of expression cassettes have been described in the art, each of which typically comprises all of the elements which allow the transcription of a DNA or DNA fragment into mRNA and the translation of the latter into protein, inside a host cell. Typically, the elements necessary for the expression of a nucleic acid in a host cell include a promoter that is functional in the selected host cell and which can be constitutive or inducible; a ribosome binding site; a start codon (ATG); a region encoding a signal peptide, necessary for the recombinant protein to be secreted; a stop codon; and a 3' terminal region (translation and/or transcription terminator). Other transcription control elements, such as enhancers, operators, and repressors can be also operatively associated with the polynucleotide to direct transcription and/or translation in the cell. The signal peptide-encoding region is preferably adjacent to the nucleic acid coding for the recombinant protein of the invention and placed in proper reading frame. The signal peptide-encoding region can be homologous or heterologous to the DNA molecule encoding the protein of interest or fusion protein of the invention and can be specific to the secretion apparatus of the host used for expression.

The open reading frame constituted by the recombinant nucleic acid of the invention, solely or together with the signal peptide, is placed under the control of the promoter so that transcription and translation occur in the host cell. Promoters and other elements necessary for the expression of a nucleic acid in a host cell are widely known and available to those skilled in the art.

Lastly, the nucleic acid sequences of the present invention may be codon optimized such that the transcription of the DNA encoding the proteins and/or the fusion proteins of the invention is enhanced and/or the translation of the mRNA encoding the proteins and/or the fusion proteins is prolonged.

A "codon-optimized DNA or mRNA sequence" means a nucleic acid sequence that has been adapted for a better expression into the host cell, by replacing one or more codons with one or more codons that are more frequently used in the genes of said host cell as described in US 2004/0209241 in the case of codon-optimized DNA sequences or to maximize the G/C content of the mRNA sequence according to the host cell used as described in US 2011/0269950 in the case of codon-optimized mRNA sequences. The codon optimization of the nucleic acid sequences is properly managed such that it does not change the amino acid sequence of the proteins and/or the fusion proteins, which are expressed in the host cells.

In another embodiment a host cell is transformed with an expression cassette of the invention. A host cell can be any cell, i.e., any eukaryotic or prokaryotic cell, into which an expression cassette can be inserted. According to the present invention, preferred host cells are eukaryotic or prokaryotic cells, including, but not limited to, animal cells (e.g., mammalian, bird, insect and fish host cells), plant cells (including eukaryotic algal cells), fungal cells, yeast cells, bacterial cells, and protist cells. Preferred prokaryote host cells useful in the invention include *Escherichia coli,* bacteria of *Bacillus* genus, *Lactococcus lactis, Pseudomonas fluorescens,* bacteria of *Caulobacter* genus, *Corynebacterium glutamicum* and *Ralstonia eutropha.* A particularly preferred prokaryote host cell for use in the present invention is *Escherichia coli.* Preferred eukaryote host cells useful in the invention include *Leishmania tarentolae, Tetrahymena thermophila, Willaertia magna,* Vero cell, CHO cell, 293 cell, 293T cell, SF9 cell, S2 cell, EB66 duck cell, *Pichia pastoris, S. cerevisiae, Hansenula polymorpha, Nicotiana benthamiana* cell, *Physcomitrella patens* cell, *Oryza sativa* cell, *Oryza glaberrima* cell, *Medicago truncatula* cell, *Zea mays* cell, *Schizochytrium* sp., *Phaeodactylum tricornutum* and *Myceliophthora thermophila.* A particularly preferred eukaryote host cell for use in the present invention is *Leishmania tarentolae* or CHO.

As glycosylation in eukaryote cells is different from and more complex than glycosylation in prokaryote cells, a protein of interest which is naturally expressed in an eukaryote cell is preferably expressed, as a fusion protein with the fragment of the lamprey VLR-B antibody according to the present invention, in an eukaryote host cell. Similarly, a protein of interest which is naturally expressed in a prokaryote cell is preferably expressed, as a fusion protein with the fragment of the lamprey VLR-B antibody according to the present invention, in a prokaryote host cell.

There are a variety of means and protocols for inserting expression cassettes into host cells including, but not limited to, transformation, transfection, cell or protoplast fusion, use of a chemical treatment (e.g., polyethylene glycol treatment of protoplasts, calcium treatment, transfecting agents such as LIPOFECTIN™ and LIPOFECTAMINE™ transfection reagents available from Invitrogen (Carlsbad, Calif.)), use of various types of liposomes, use of a mechanical device (e.g., nucleic acid coated microbeads), use of electrical charge (e.g., electroporation), and combinations thereof. It is within the skill of a practitioner in the art to determine the particular protocol and/or means to use to insert a particular vector molecule described herein into a desired host cell.

Recombinant host cells may be grown under a variety of specified conditions as determined by the requirements of the cells. For example, a host cell may possess certain nutritional requirements or a particular resistance or sensitivity to physical (e.g. temperature) and/or chemical (e.g. antibiotic) conditions. In addition, specific culture conditions may be necessary to regulate the expression of a desired gene (e.g. the use of inducible promoters). These varied conditions and the requirements to satisfy such conditions are understood and appreciated by practitioners in the art.

Methods for the purification of proteins are well-known to the skilled person. The obtained recombinant protein or fusion protein can be purified from lysates and cell extracts, from the culture medium supernatant, by methods used individually or in combination, such as fractionation, chromatographic methods, immunoaffinity methods using specific mono- or polyclonal antibodies, etc. Preferably the obtained recombinant protein or fusion protein is purified from the culture medium supernatant.

Another embodiment is directed to a molecule or a recombinant protein of the invention which is capable of forming a stable multimer. In a preferred embodiment, the stable multimer of the present invention is a stable homo-multimeric recombinant protein comprising a protein selected from the group consisting of the ectodomain of an influenza HA protein, a *Shigella* IpaD protein and a *Shigella* MxiH protein fused to a protein having an amino acid sequence which has at least 80% identity to SEQ ID NO: 1. In particular, the stable homo-multimeric recombinant protein comprises a protein selected from the group consisting of the ectodomain of an influenza HA protein, a *Shigella* IpaD protein and a *Shigella* MxiH protein fused to a protein having an amino acid sequence which has at least 85% identity, at least 90% identity, at least 95% identity, at least 97% identity, at least 98% identity, at least 99% identity or even 100% identity to SEQ ID NO: 1. Preferably the protein is influenza HA protein.

According to another preferred embodiment, the stable multimer of the present invention is a stable homo-multimeric recombinant protein comprising a protein selected from the group consisting of the ectodomain of an influenza HA protein, a *Shigella* IpaD protein and a *Shigella* MxiH protein fused to a protein having an amino acid sequence which has at least 80% identity to SEQ ID NO: 2. In particular, the stable homo-multimeric recombinant protein comprises a protein selected from the group consisting of the ectodomain of an influenza HA protein, a *Shigella* IpaD protein and a *Shigella* MxiH protein fused to a protein having an amino acid sequence which has at least 85% identity, at least 90% identity, at least 95% identity, at least 97% identity, at least 98% identity, at least 99% identity or even 100% identity to SEQ ID NO: 2. Preferably the protein is influenza HA protein.

In a preferred aspect of these embodiments of the invention (i.e. the stable multimers), the 7 cysteines which correspond to positions 2, 7, 13, 19, 21, 24 and 27 of SEQ ID NO: 1 (or the 8 cysteines which correspond to positions 2, 15, 20, 26, 32, 34, 37 and 40 of SEQ ID NO: 2) are conserved in the amino acid sequence of the protein which is derived from the C-terminus of a Lamprey VLR-B and which is fused to a protein selected from the group consisting of the ectodomain of an influenza HA protein, a *Shigella* IpaD protein and a *Shigella* MxiH protein. In some embodiments a linker may be inserted between the amino acid sequence of the protein selected from the group consisting of the ectodomain of an influenza HA protein, a *Shigella* IpaD protein and a *Shigella* MxiH protein and the fused amino acid sequence.

Preferably, the stable multimers of the invention do not comprise a leucine-rich repeat (LRR) module from a lamprey VLR-B antibody. In particular, a stable multimer as described herein does not comprise an amino acid sequence having the sequence of SEQ ID NO: 29. Preferably, a stable multimer of the invention does not comprise one or more of an LRRNT module, an LRR1 module, an LRRV module, an LRRCT module, a CP and a Stalk region from a lamprey VLR-B antibody. Preferably, the only lamprey-derived amino acid sequence which is present within a stable multimer of the present invention is derived from the extreme C-terminus of a lamprey VLR-B antibody (i.e. the section of the protein C-terminal to the Stalk region, see FIG. 11C of WO 2008/016854). Preferably, the only lamprey-derived amino acid sequence which is present in a stable multimer of the present invention is a sequence having at least 80% identity to SEQ ID NO: 1 or SEQ ID NO: 2, for example at least 85% identity, at least 90% identity, at least 95% identity, at least 97% identity, at least 98% identity, at least 99% identity or even 100% identity to SEQ ID NO: 1 or SEQ ID NO: 2.

The invention also provides a stable homo-multimeric recombinant protein produced by an expression system from a nucleic acid molecule comprising a nucleic acid sequence encoding a protein selected from the group consisting of the ectodomain of an influenza HA protein, a *Shigella* IpaD protein and a *Shigella* MxiH protein fused to a nucleic acid sequence having at least 80% identity to SEQ ID NO: 3. In particular, the stable homo-multimeric recombinant protein is produced by an expression system from a nucleic acid molecule comprising a nucleic acid sequence encoding a protein selected from the group consisting of the ectodomain of an influenza HA protein, a *Shigella* IpaD protein and a *Shigella* MxiH protein fused to a nucleic acid sequence having has at least 85% identity, at least 90% identity, at least 95% identity, at least 97% identity, at least 98% identity, at least 99% identity or even 100% identity to SEQ ID NO: 3. Preferably the nucleic acid sequence encodes an influenza HA protein.

In some embodiments, the stable homo-multimeric recombinant protein is produced by an expression system from a nucleic acid molecule comprising a nucleic acid sequence encoding a protein selected from the group consisting of the ectodomain of an influenza HA protein, a *Shigella* IpaD protein and a *Shigella* MxiH protein fused to a nucleic acid sequence with at least 80% identity to SEQ ID NO: 4. In particular, the stable homo-multimeric recombinant protein is produced by an expression system from a nucleic acid molecule comprising a nucleic acid sequence encoding a protein selected from the group consisting of the ectodomain of an influenza HA protein, a *Shigella* IpaD protein and a *Shigella* MxiH protein fused to a nucleic acid sequence having has at least 85% identity, at least 90% identity, at least 95% identity, at least 97% identity, at least 98% identity, at least 99% identity or even 100% identity to SEQ ID NO: 4. Preferably the nucleic acid sequence encodes an influenza HA protein.

In a preferred aspect of these embodiments of the invention, the nucleic acid sequence which encodes the amino acid sequence derived from the C-terminus of a Lamprey VLR-B antibody (and which is fused to a nucleic acid sequence coding for a protein selected from the group consisting of the ectodomain of an influenza HA protein, a *Shigella* IpaD protein and a *Shigella* MxiH protein) encodes an amino acid sequence which comprises cysteine residues at positions within said amino acid sequence that correspond to positions 2, 7, 13, 19, 21, 24 and 27 of SEQ ID NO: 1 (or comprises cysteine residues at positions within said amino acid sequence that correspond to positions 2, 15, 20, 26, 32, 34, 37 and 40 of SEQ ID NO: 2). In some embodiments a spacer nucleic acid sequence coding for a peptide linker may be inserted between nucleic acid sequence coding for a protein selected from the group consisting of the ectodomain of an influenza HA protein, a *Shigella* IpaD protein and a *Shigella* MxiH protein and the fused nucleic acid sequence.

The invention also provides a pharmaceutical composition comprising a molecule or a recombinant protein of the invention and a pharmaceutically acceptable carrier or diluent. In a preferred embodiment, an immunogenic composition comprises a molecule or a recombinant protein of the invention. The molecule or the recombinant protein of the invention may also be for use as a medicament. In a preferred embodiment the molecule or the recombinant protein of the invention is for use in inducing an immune response to an antigen in a subject. In another preferred embodiment, a molecule or a recombinant protein, comprising an influenza antigen according to the invention, is for use in inducing an immune response against influenza virus. In a more preferred embodiment, the recombinant influenza HA protein according to the invention is for use in inducing an immune response against influenza virus. In another preferred embodiment, the immunogenic composition of the invention is a vaccine composition.

The pharmaceutical composition and the immunogenic composition of the invention may be formulated as conventional pharmaceutical or vaccine preparations. This can be done using standard pharmaceutical or vaccine formulation chemistries and methodologies, which are available to those skilled in the art. Any solvent, dispersing medium, charge, adjuvant, etc., commonly used in the formulation of pharmaceuticals and vaccines to enhance stability, sterility, potency or deliverability of the active agent, which does not produce any secondary reaction, for example an allergic reaction, especially in humans, may be used. The excipient is selected on the basis of the pharmaceutical or vaccine form chosen, the method and the route of administration. Appropriate excipients, and requirements in relation to pharmaceutical formulation, are described in "Remington's Pharmaceutical Sciences" (19th Edition, A. R. Gennaro, Ed., Mack Publishing Co., Easton, Pa. (1995)), which represents a reference work in the field. Examples of pharmaceutically acceptable excipients are water, phosphate-buffered saline solutions and 0.3% glycine solution.

The pharmaceutical compositions and the immunogenic compositions may be sterilized by conventional sterilization techniques, or may be sterile filtered. The resulting aqueous solutions may be packaged and stored in liquid form or lyophilized, the lyophilized preparation being reconstituted with a sterile aqueous carrier prior to administration. In a preferred embodiment the pharmaceutical compositions and the immunogenic compositions are packaged and stored as micropellets via a prilling process as described in WO2009109550. The pH of the preparations typically will be between 3 and 11, e.g., between 5 and 9, 6 and 8, or 7 and 8, such as 7 to 7.5.

Once formulated or reconstituted, the pharmaceutical compositions and the immunogenic compositions can be delivered to a subject in vivo using a variety of known routes and techniques. For example, the liquid preparations can be provided as an injectable solution, suspension or emulsion and administered via parenteral, subcutaneous, intradermal, intramuscular, intravenous injection using a conventional needle and syringe, or using a liquid jet injection system. Liquid preparations can also be administered topically to skin or mucosal tissue, or provided as a finely divided spray suitable for respiratory or pulmonary administration. Other modes of administration include oral administration, suppositories, and active or passive transdermal delivery techniques.

For oral administration, the pharmaceutical compositions and the immunogenic compositions may be formulated as, for example, a capsule, a tablet, a suspension, or a liquid.

The pharmaceutical compositions and the immunogenic compositions may also be prepared in a solid form (including granules, micropellets, powders or suppositories).

Another embodiment is directed to method for treating a patient, said method comprising administering to said patient a pharmaceutical composition of the invention. A preferred embodiment contemplates a method for inducing an immune response to an antigen in a patient, said method comprising administering to said patient an immunogenic composition or a vaccine composition, of the invention.

Another embodiment is directed to a method for multimerizing a recombinant protein comprising:

a) fusing a nucleic acid sequence having at least 80% identity to SEQ ID NO: 3 to the nucleic acid sequence coding for said recombinant protein, with the proviso that said recombinant protein is not a lamprey VLR-B antibody protein,
b) expressing the fusion protein encoded by said nucleic acid sequence, under conditions which lead to the multimerization of said recombinant protein.

These conditions are known by the skilled person and essentially consist of avoiding extreme conditions, e.g. high concentration of solutes, extremes of pH, mechanical forces and the presence of chemical denaturants.

Another embodiment is directed to a method for multimerizing a recombinant protein comprising:

a) fusing a nucleic acid sequence having at least 80% identity to SEQ ID NO: 4 to the nucleic acid sequence coding for said recombinant protein, with the proviso that said recombinant protein is not a lamprey VLR-B antibody protein,
b) expressing the fusion protein encoded by said nucleic acid sequence, under conditions which lead to the multimerization of said recombinant protein.

In a preferred embodiment the method is for multimerizing an antigen, an antibody or a scaffold. In a most preferred embodiment the method is for multimerizing a recombinant influenza HA or HA ectodomain protein.

EXAMPLE 1

Polymerization of a Recombinant Influenza HA Ectodomain Protein

Two sequences derived from the C-terminus of VLR-B antibodies of lamprey were evaluated through fusion to the C-terminus of the HA protein. The first tested sequence was SEQ ID NO: 1 and the second tested sequence was SEQ ID NO: 2. SEQ ID NO: 1 is a shortened version of SEQ ID NO: 2. SEQ ID NO: 1 corresponds to the 30 amino acids at the extreme C-terminus of VLR-B antibodies of Lamprey and SEQ ID NO: 2 corresponds to the 43 amino acids at the extreme C-terminus of VLR-B antibodies of Lamprey (see FIG. 11C of WO 2008/016,854). By extreme C-terminus it is meant the portion of the VLR-B C-terminal to the Stalk region.

A third sequence tested was the foldon sequence of the T4 phage (SEQ ID NO: 5).

The nucleic acid sequence coding for the HA ectodomain from influenza strain A/California/07/09 (H1N1), (which comprised its own signal sequence, but which did not comprise the sequences of the transmembrane and cytoplasmic tail regions of HA), was optimized for codon usage in *Leishmania tarentolae* by Geneart (Regensburg, Germany). This sequence is referred to herein as SEQ ID NO: 10.

The nucleic acid sequences coding for the three tested multimerization sequences (i.e. the two sequences derived from the C-terminus of the VLR-B antibody and the T4 phage foldon sequence) were individually fused to the nucleic acid sequence SEQ ID NO: 10 (which encodes the ectodomain of the HA protein from influenza strain A/California/07/2009) by Geneart (Regensburg, Germany). Accordingly, SEQ ID NO: 7 is the nucleic acid sequence SEQ ID NO: 3 (which is the nucleic acid sequence encoding the amino acid sequence SEQ ID NO: 1, i.e. the shortened fragment of the lamprey VLR-B antibody according to the present invention) fused to the nucleic acid sequence SEQ ID NO: 10. SEQ ID NO: 8 is the nucleic acid sequence SEQ ID NO: 4 (which is the nucleic acid sequence encoding the amino acid sequence SEQ ID NO: 2, i.e. the "long" (not shortened) fragment of the lamprey VLR-B antibody according to the present invention) fused to the nucleic acid sequence SEQ ID NO: 10 and SEQ ID NO: 9 is the nucleic acid sequence SEQ ID NO: 6 (which is the nucleic acid sequence encoding the amino acid sequence SEQ ID NO: 5, i.e. the foldon sequence of the T4 phage) fused to the nucleic acid sequence SEQ ID NO: 10.

Figure 1:
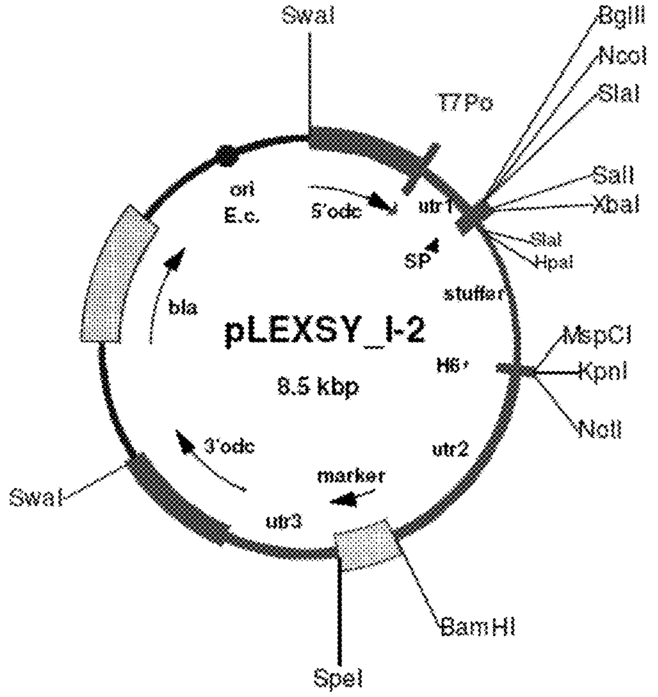
FIG. 1 shows expression cassettes used to produce recombinant influenza HA ectodomain proteins.
Figure 1:
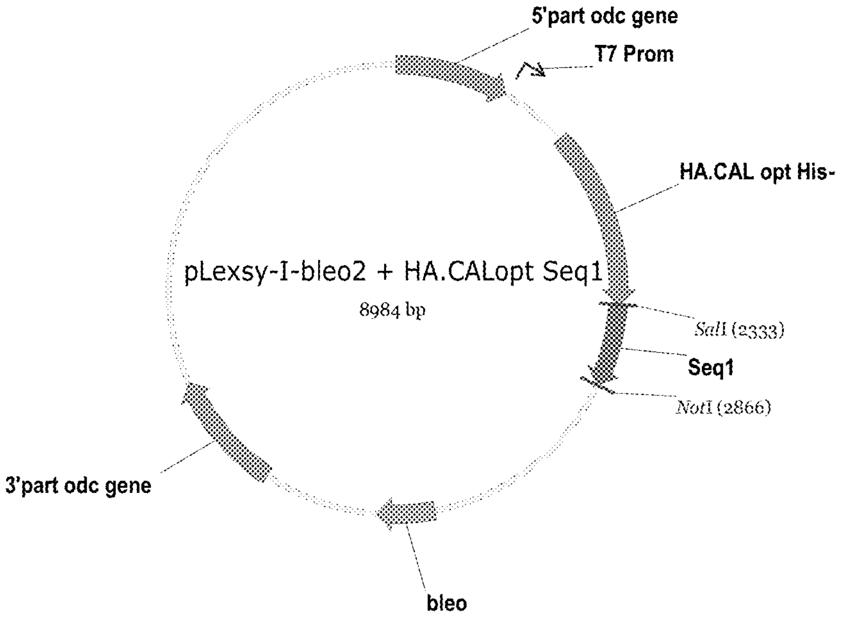
Figure 1:
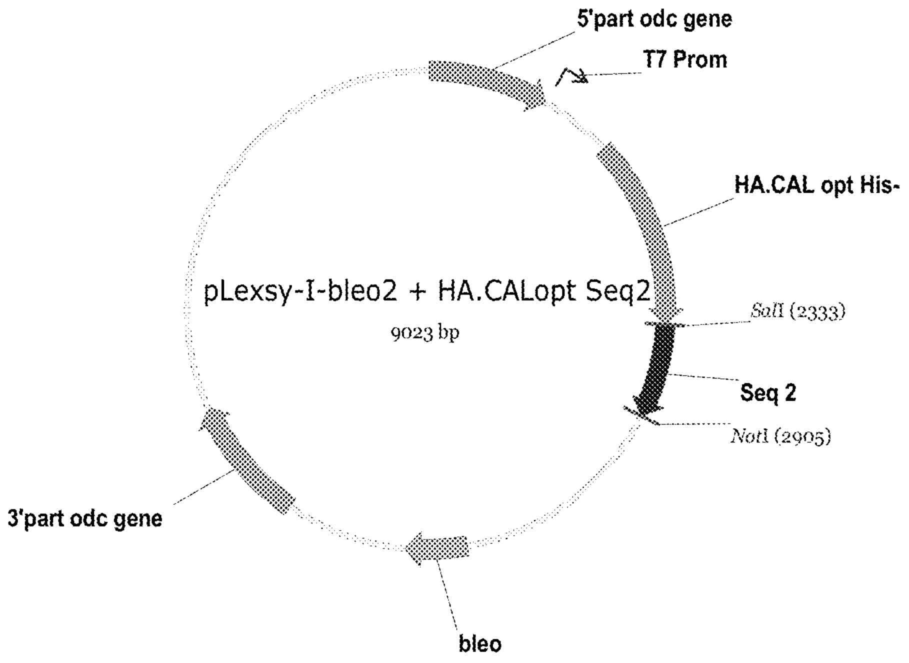
Figure 1:
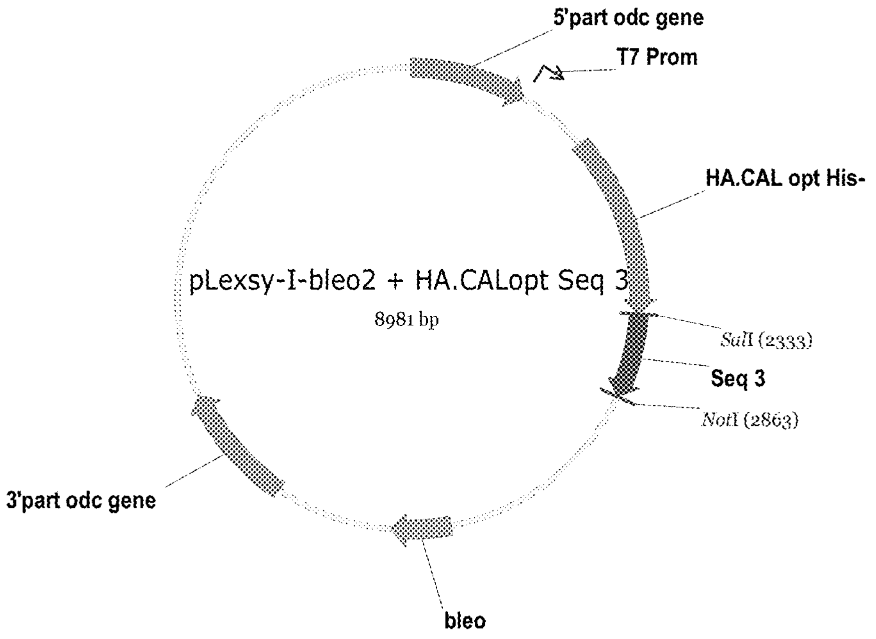

SEQ ID NO: 7, SEQ ID NO: 8 and SEQ ID NO: 9 were each separately inserted into the SalI/NotI restriction site of the pLexsy-I-bleo2 expression cassette as shown in FIG. 1. SEQ ID NO: 10 was inserted into the NcoI/NotI restriction site of the pLexsy-I-bleo2 expression cassette. This expression cassette allows the integration of the gene of interest into the chromosomal ornithine decarboxylase (odc) locus of the *Leishmania tarentolae* T7-TR recipient strain (Kushnir et al., Protein Expr. Purif., 42(1), 37-46 (2005)), that constitutively expresses bacteriophage T7 RNA polymerase and TET repressor under the control of host RNA polymerase I. Induction of the expression of the protein of interest is carried out via the T7 promoter inducible by tetracycline addition (user's guide EGE-1400, Jena Bioscience, Jena, Germany).

The expression cassettes containing the HA sequence with or without one of the polymerization sequences were then digested by SwaI, and 1 μg of each purified linear SwaI fragment was, in separate experiments, transfected into the *L. tarentolae* T7-TR host strain via nucleoporation using the Nucleofector II device (Amaxa Biosystems, Cologne, Germany) and following the instructions of the Basic Parasite Nucleofector™ Kit 1 (Lonza, Bale, Switzerland). The transfected cells were transferred into 10 ml of BHI (Brain-Heart Infusion) medium (Jena Bioscience) containing 5 μg/ml Hemin, 50 units/ml penicillin, 50 μg/ml streptomycin (Pen/Strep to avoid bacterial contamination), 100 μg/ml nourseothricin (NTC) and 100 μg/ml hygromycin (NTC/Hygro: for maintaining T7 polymerase and TET repressor genes respectively in the T7-TR host) and incubated overnight at 26° C. in the dark. Twenty-four hours post transfection, a 2 ml aliquot of the suspension was centrifuged for 5 min at 2000 g, the pellet was resuspended in 50-100 μl of BHI medium and the cells were gently plated on fresh BHI-agar plates containing antibiotics plus 100 μg/ml of bleomycin (selective growth medium) for the selection of recombinant parasites. Approximately 7-9 days after plating, small colonies were visible and transferred to 0.2 ml of selective growth medium. Each recombinant clone of parasites was expanded into 10 ml of selective medium in a shake flask at 26° C.

Confirmation of the integration of the expression cassette containing HA sequences into the genome was performed by diagnostic PCR following the Jena Bioscience recommendation.

The confirmed recombinant parasites were cultivated in 100 ml BHI medium supplemented as described above with Hemin and antibiotics at 26° C., and agitated at 100 rpm in the dark. In order to induce the production of the rHA protein, the T7 driven transcription was induced by addition of 10 μg/ml of Tetracycline into the supplemented medium at the time of inoculation of the parasites.

For fermentation, 1 liter Biostat Qplus 12 fermenters (Sartorius AG, Aubagne, France), were used. Briefly 700 ml of supplemented BHI medium was inoculated with 1/10 of a recombinant parasite starter culture in exponential growth (0.4 $OD_{600}$) and cultivated in the dark at 26° C., 100 rpm, 40% $pO_2$, pH 7.4±0.1. Culture parameters were recorded using the MFCS/WIN software (Sartorius AG). Induction using 10 μg/ml of Tetracycline was performed in parallel with inoculation of the recombinant parasites (as was done for the shake flask cultures). Regulation of the pH with HCl 1N/NaOH 1N, and infusion of a 100 g/L solution of glucose at 1.5 ml/h began 43 h after induction while P1860 anti protease cocktail (1/800, Sigma, Saint Quentin Fallavier, France) was added at the same time.

Samples of the culture were taken every day in order to determine the optical density ($OD_{600}$) of the culture (one OD600 is equivalent to approximately $1.5\times10^7$ parasites/ml), the concentration of various metabolites (Gln, Glu, Gluc, Lac, $NH_4^+$), and the cell mobility by microscopy.

After 48 h, the supernatants of the transformed *Leishmania tarentolae* cultures were collected and filtered on a 0.2 μm filter. Proteins were quantified in the samples by optical density measurement at 595 nm and samples were normalized.

20 μl of each sample was loaded and run on a SDS-PAGE gel (NuPAGE® Novex Bis Tris 4-12%, Life Technologies, Carlsbad, USA). The supernatant from a transformed *Leishmania tarentolae* culture cultivated over 48 h in the absence of the transcription inductor tetracycline served as a negative control.

To test the thermal stability of the different recombinant HA proteins obtained using the different expression plasmids, the three test samples and the negative control sample were divided in two, with one half of the sample being heated to 99° C. for 15 minutes using a heating block before migration on the SDS-PAGE gel, and the other half not being heated before migration on the SDS-PAGE gel. A further control sample on the gel contained a heated culture supernatant of *Leishmania tarentolae* (15 minutes at a temperature of 99° C.) transformed with a plasmid expressing another protein (i.e. an antibody against influenza).

A Western Blot of the SDS-PAGE gel was made using a nitrocellulose membrane (BioRad Laboratories, Hercules, USA), followed by a treatment with PBS, Tween 20 0.1% and milk 5% (DIFCO-BD, Sparks, USA) in order to block non-specific fixation sites.

The blot was probed using a rabbit polyclonal antibody against influenza A/California/07/09 HA, with a titer of 8000 (inhibition of haemagglutination) and a titer of 32 000 (seroneutralization), followed by an anti-rabbit IRDdye800CW antibody (Li-Cor BioSciences, Lincoln, USA) and the OPTI-4CN™ (BioRad Laboratories) substrate. The Western Blot was analyzed with an ODYSSEY (Li-Cor BioSciences) imaging system.

The results of the Western Blot are shown in FIG. 2. The results were really remarkable. Firstly, whilst the HA protein fused to the T4 foldon sequence (SEQ ID NO: 5, lanes 11-12) was only in trimeric form, the HA protein fused to the lamprey VLR-B antibody C-terminal domain SEQ ID NO: 1 (lanes 7-8), or to the lamprey VLR-B antibody C-terminal domain SEQ ID NO: 2 (lanes 9-10), were produced not only as trimers but also as tetramers, pentamers and other higher polymerized forms. In addition, the HA proteins fused to the VLR-B antibody C-terminal sequences were mostly secreted into the supernatant of the culture, as very little or no HA was detected intracellularly and no lysis was observed (results not shown). The secretion of a recombinant protein into the culture supernatant is highly advantageous for downstream purification when compared with purification of a recombinant protein that remains inside the host cell. Furthermore, it can be seen that the polymers obtained from the HA protein fused to either one of the tested lamprey VLR-B antibody C-terminal domains were stable following heat treatment (lanes 7 and 9), while the HA protein fused to the T4 foldon sequence lost its trimeric form after heat treatment (lane 11). The thermal stability of the polymers obtained from the HA protein fused to one of the lamprey VLR-B antibody C-terminal domains tested is of great interest, since increased stability should increase the shelf-life of an immunogenic composition containing such an antigen. Furthermore, a thermostable recombinant protein antigen is also expected to have a longer in vivo stability when injected into a patient.

EXAMPLE 2

Immunogenicity Study of a Recombinant Influenza HA Protein Polymerized by Fusion to a Lamprey VLR-B Antibody C-Term Domain Recombinant HA ectodomain protein polymerized by fusion to the lamprey VLR-B antibody C-term domain SEQ ID NO: 2 (rHA poly) was produced as described in example 1.

After 72 h of induction with tetracycline in the medium of the *L. tarentolae* culture, shake flask harvests were performed and centrifuged for 30 min at 5,000 g. After concentration and diafiltration on a Sartorius sartocon slice 200 cassette, supernatants were placed on a Con A Sepharose 4B column of 1 ml. The recombinant HA was eluted using a 0.5M alpha-D-Methylmannoside in PBS-MM buffer. The eluate was dialysed against PBS/tween, concentrated on Ultracell 10K and filtered with a 0.22 μm filter. The recombinant HA was titrated by the microbradford technique. Each sample was resuspended in PBS+Tween 0.005%.

Two groups of 10 female Balb/C ByJ mice aged 8 weeks received two immunizations, one on day 0 and one on day 28, via the intramuscular (IM) route, of either 10 μg of influenza A/California/07/2009 rHA ectodomain protein polymerized by fusion to the lamprey VLR-B antibody C-term domain SEQ ID NO: 2 (rHA poly) (produced as described in example 1), or 10 μg of influenza A/California/07/2009 rHA ectodomain monomeric protein (rHA mono) produced in *Leishmania tarentolae* transformed with a plasmid expressing only the rHA ectodomain, i.e. not fused to a polymerization sequence (SEQ ID NO: 11). The 10 μg rHA proteins were resuspended in a Buffer (PBS+Tween 0.005%) and the volume injected was 2×50 μl (100 μl in total).

Finally, 5 female Balb/C ByJ mice aged 8 weeks received 100 μl of Buffer (2×50 μl).

Three weeks after the booster injection, blood samples were taken under anesthesia at D49 from all the animals. The anesthesia was performed by Imalgene® (1.6 mg of Ketamine) and Rompun (0.32 mg of Xylazine) administered in a volume of 200 μl via the intraperitoneal route. 1 ml of blood was collected in vials containing clot activator and serum separator (BD Vacutainer SST ref 367783). After a single night at +4° C. or one hour at 37° C., the blood was centrifuged at 10,000 rpm for 5 minutes or 3,000 rpm for 20 minutes and the serum was stored at −20° C. until analysis.

The presence of haemagglutination inhibitory antibodies against the influenza A/California/07/09 (H1N1) strain was assessed using chicken red blood cells (cRBCs). Assays were performed on individual Receptor Destroying Enzyme (RDE) treated serum samples and titers were expressed as the reciprocal of the highest dilution showing no haemagglutination, as described by Kendal et al., Haemagglutination inhibition, in Concepts and procedures for laboratory-based influenza surveillance, US Department of Health and Human Services and Pan-American Health Organization, Atlanta, Ga., 1982, pp. B17-B35.9.

The results of the inhibition of haemagglutination assay are shown in FIG. 3. The hemaggutination-inhibition (HAI) titers obtained by immunization of mice with a polymeric rHA ectodomain are significantly higher than those obtained by immunization of mice with a monomeric rHA ectodomain. Table 1 shows that the polymeric rHA ectodomain, obtained by fusion of influenza A/California/07/2009 rHA ectodomain protein to the lamprey VLR-B antibody C-term domain SEQ ID NO: 2, is 4 times more immunogenic than the influenza A/California/07/2009 monomeric rHA ectodomain.

TABLE I

| HAI titers | | | | |
|---|---|---|---|---|
| Group # | IM immunization | Mouse | HAI_D50 | Geo mean |
| B | Buffer#2 - 100 μl | 6 | 5 | 5 |
| | | 7 | 5 | |
| | | 8 | 5 | |
| | | 9 | 5 | |
| | | 10 | 5 | |
| F | rHA poly 10 μg | 41 | 320 | 422 |
| | | 42 | 2560 | |
| | | 43 | 160 | |
| | | 44 | 160 | |
| | | 45 | 640 | |
| | | 46 | 1280 | |
| | | 47 | 640 | |
| | | 48 | 320 | |
| | | 49 | 160 | |
| | | 50 | 320 | |
| G | rHA mono 10 μg | 51 | 320 | 106 |
| | | 52 | 80 | |
| | | 53 | 20 | |
| | | 54 | 2560 | |
| | | 55 | 80 | |
| | | 56 | 40 | |
| | | 57 | 40 | |
| | | 58 | 40 | |
| | | 59 | 160 | |
| | | 60 | 160 | |

EXAMPLE 3

Polymerization of a Recombinant Influenza HA Ectodomain Protein Expressed in CHO Cells The polymerization of recombinant influenza HA ectodomain protein via fusion with the lamprey sequences was also tested in another host cell.

The nucleic acid sequence coding for the HA ectodomain from influenza strain A/California/04/09 (H1N1) (Genbank Accession Number FJ966082), which comprised its own signal sequence, but which did not comprise the sequences of the transmembrane and cytoplasmic tail regions of HA, was optimized for codon usage in CHO by Geneart (Regensburg, Germany). This sequence is referred to herein as SEQ ID NO: 12.

The nucleic acid sequences coding for the three tested multimerization sequences (i.e. the two sequences derived from the C-term of the VLR-B antibody and the T4 phage foldon sequence), optimized for codon usage in CHO, were individually fused to the nucleic acid sequence SEQ ID NO: 12. Accordingly, SEQ ID NO: 13 is the nucleic acid sequence SEQ ID NO: 3 fused to the nucleic acid sequence SEQ ID NO: 12. SEQ ID NO: 14 is the nucleic acid sequence SEQ ID NO: 4 fused to the nucleic acid sequence SEQ ID NO: 12 and SEQ ID NO: 15 is the nucleic acid sequence SEQ ID NO: 6 fused to the nucleic acid sequence SEQ ID NO: 12. SEQ ID NO: 26 is the protein sequence encoded by SEQ ID NO: 13. SEQ ID NO: 27 is the protein sequence encoded by SEQ ID NO: 14. SEQ ID NO: 28 is the protein sequence encoded by SEQ ID NO: 15.

SEQ ID NO: 12, SEQ ID NO: 13, SEQ ID NO: 14 and SEQ ID NO: 15 were each separately inserted into the HindIII/EcoRI restriction site of the pEE14.4 expression cassette shown in FIG. 4. With this expression cassette no induction is needed as the recombinant proteins are constitutively expressed.

The expression cassettes containing the HA sequence with or without one of the polymerization sequences were transfected into a CHO host cell (CHOK169 ATCC Number CB-CCL-61pUnK). 10 μg of each plasmid was separately introduced into $10\times10^6$ CHO cells via nucleoporation using the Nucleofector II device (Amaxa Biosystems, Cologne, Germany). The CHO cells were then plated on 2 ml of Ex-Cell® CHO fusion animal component free medium (SAFC Biosciences Sigma-Aldrich) containing 4 mM of L-glutamine at 37° C. The cultures were statically maintained at 37° C. under 5% $CO_2$ for 24 h and then with agitation (100 rpm) for 48 h.

72 h after nucleoporation, the supernatants of the transformed CHO cultures were collected by centrifugation for 10 seconds at 10,000 rpm.

15 μl of each sample mixed with 5 μl NuPAGE® LDS Sample Buffer (4×) (Life Technologies) was loaded and run on a SDS-PAGE gel (NuPAGE® Novex 3-8% Tris-Acetate, Life Technologies, Carlsbad, USA). The supernatant from a CHO culture that was electroporated in the absence of any expression cassette served as a negative control. 20 μl of HiMark™ Pres stained High molecular Weight Protein Standard (LC5699 Life technlologies) was used as a molecular weight marker.

Sample separation was performed at 150V in Tris-acetate Buffer for 40 minutes (Life Technologies).

A Western Blot of the SDS-PAGE gel was made using a nitrocellulose membrane (BioRad Laboratories, Hercules, USA), followed by an overnight treatment with PBS and milk 5% (DIFCO-BD, Sparks, USA) in order to block non-specific fixation sites.

The blot was probed using a rabbit polyclonal antibody against influenza A/California HA diluted at 1/1000 in PBS, for 1 h at room temperature. The blot was then washed three times with PBS and Tween 20 0.05% before incubation with an anti-rabbit IRDdye800 sheep antibody (Rockland, Limerick, USA) diluted at 1/5000 in PBS. The Western Blot was analyzed with an ODYSSEY (Li-Cor BioSciences) imaging system.

The results of the Western Blot are shown in FIG. 5. The results were again remarkable. Firstly, whilst the HA protein fused to the T4 foldon sequence was only in a dimeric or a trimeric form, the HA protein fused to the lamprey VLR-B antibody C-terminal domain SEQ ID NO: 1 (short lamprey sequence), or to the lamprey VLR-B antibody C-terminal domain SEQ ID NO: 2 (long lamprey sequence), were produced not only as dimers or trimers but also as tetramers, pentamers and other higher polymerized forms. In addition, the HA proteins were secreted into the supernatant of the culture, as the Blot was conducted on the supernatant of the cultures. The secretion of a recombinant protein into the culture supernatant is highly advantageous for downstream purification when compared with purification of a recombinant protein that remains inside the host cell.

EXAMPLE 4

Polymerization of a Recombinant *Shigella flexneri* IpaD Protein Expressed in *E. coli*

The nucleic acid sequence coding for the IpaD protein from *Shigella flexneri* Serotype 2a Strain 301 (Q. Jin et al., Nucleic Acids Research, 30 (20), 4432-4441 (2002), Genbank Accession Number AF386526), was optimized for codon usage in *E. coli* by Geneart (Regensburg, Germany). This sequence is referred to herein as SEQ ID NO: 16.

SEQ ID NO: 16 was fused to the nucleic acid sequence SEQ ID NO: 4 also codon optimized for *E. coli* by Geneart (Regensburg, Germany) to generate SEQ ID NO: 17. The corresponding protein sequence is SEQ ID NO: 18. SEQ ID NO: 16 and SEQ ID NO: 17 were also fused to a sequence coding for a polyhistidine-tag (6×His) via a GGSLE linker, thus generating SEQ ID NO: 19 (IpaD-His, the GGSLE linker is between the IpaD sequence and the His-tag) and SEQ ID NO: 20 (IpaD-lamprey-His, the GGSLE linker is between the IpaD-lamprey sequence and the His-tag) respectively.

SEQ ID NO: 16, SEQ ID NO: 17, SEQ ID NO: 19 and SEQ ID NO: 20 were each separately inserted into the NcoI/XhoI restriction site of the pM1800 expression cassette as shown in FIG. 6. Induction of the expression of the protein of interest is carried out via addition of IPTG.

5 μg of the plasm ids containing the IpaD sequence with or without the polymerization sequence and with or without the linker and His-tag sequence were suspended in 10 μl of water. 0.5 μl of the suspension corresponding to the IpaD sequence with or without the polymerization sequence and without the linker and His-tag sequence was added to cultures of either *E. coli* BL21 DE3 C6000-03 (Life Technologies) or *E. coli* Shuffle (B) ref C3029H (New England Biolabs, i.e. *E. coli* engineered to promote the formation of disulfide bonds within proteins). 0.5 μl of the suspensions corresponding to the IpaD sequence with or without the polymerization sequence but with the linker and His-tag sequence were added to *E. coli* Shuffle (B). After mixing, the samples were placed on ice for 15 minutes. Then the samples were heat shocked at 42° C. for 30 seconds. The samples were then placed on ice for 2 minutes before dilution with 500 μl of room temperature S.O.C. Medium (Thermofisher). The samples were then incubated at 37° C. for 60 minutes before vigorous shaking (250 rpm).

100 μl of each sample was diluted and spread onto a LB medium containing Kanamycin (25 μg/ml) plate and incubated overnight at 37° C. A colony from each transformation plate was picked using a sterile inoculation loop and added to 2 ml LB broth/kanamycin 25 μg/ml. The cultures were then diluted in 25 ml of LB+Kanamycin (25 μg/ml) medium in order to obtain an optical density for seeding of $OD_{600}$=0.05.

After 2 h of growth at 37° C. with agitation (200 rpm), when the cultures reached a $OD_{600}$ of 0.4-0.8, the production of the recombinant protein was induced by IPTG 1 mM (i.e. addition of 25 μl of IPTG 1M).

The bacteria were maintained at 37° C. for about 4 h with agitation. One $OD_{600}$ unit is taken from each Erlen flask and centrifuged. After removal of the supernatants, the pellet was stored at −20° C.

The pellets were resuspended in 75 μl of Tris EDTA (10 mM Tris, 1 mM EDTA, pH 8.0, Novagen)+1 μl of Ready lyse 35 KU/μl (Epicentre) diluted at 1/50+1 μl of Benzonase 25 U/μl (Novagen). The samples were then agitated for 20 minutes at 37° C. before adding 25 μl of NuPAGE® LDS Sample Buffer (4×) (Invitrogen). 20 μl of each sample was loaded and run on SDS-PAGE gels (NuPAGE® Novex® 3-8% Tris-Acetate, Life Technologies, Carlsbad, USA). 15 μl of HiMark™ Pres stained High molecular Weight Protein Standard (LC5699 Life technlologies) was used as a molecular weight marker.

pM1800 containing no IpaD sequence, inserted in the *E. coli* induced by IPTG, served as a negative control. Sample separation was performed at 150V in Tris-acetate Buffer for 1 hour (Life Technologies).

Western Blots of the SDS-PAGE gels were made using nitrocellulose membranes (BioRad Laboratories, Hercules, USA), followed by a treatment for 1 h with PBS and milk 5% (DIFCO-BD, Sparks, USA).

The blots were probed using a mouse monoclonal antibody against IpaD, followed by an Alexa fluor Goat anti-mouse antibody (Invitrogen) or an anti-mouse IRDye 800 antibody (Rockland) diluted at 1/5000 in PBS. The Western Blots were analyzed with an ODYSSEY (Li-Cor BioSciences) imaging system.

The results of the Western Blots are shown in FIGS. 7 and 8. They are similar to the ones observed with rHA in examples 1 and 3 above. Indeed, FIG. 7 shows that while the IpaD protein without the lamprey sequence is expressed as a dimer (IpaD monomer has an expected molecular weight of 36.6 kDa), the IpaD protein fused to the lamprey VLR-B antibody C-terminal domain SEQ ID NO: 2 was produced not only as a dimer but also as trimers, tetramers, pentamers and other higher polymerized forms (the fusion IpaD-lamprey monomer has an expected molecular weight of 41.2 kDa). The polymerized IpaD proteins were produced at the highest quantities in the Shuffle *E. coli* strain.

The results in FIG. 8 show that the addition of a His-Tag, useful for downstream purification of the recombinant protein, has no detrimental effect on the polymerization of the IpaD protein by the lamprey VLR-B antibody C-terminal domain SEQ ID NO: 2.

To test the thermal stability of the different recombinant IpaD proteins obtained, a further SDS-PAGE and Western Blot was conducted as described above, except that the test samples and the negative control sample were heated to 95° C. for 10 minutes using a heating block before migration on the SDS-PAGE gel.

The results of this Western Blot are shown in FIG. 9. It can be seen that the polymers obtained from the IpaD protein fused to the lamprey VLR-B antibody C-terminal domain SEQ ID NO: 2 were stable following heat treatment.

The thermal stability of the polymers obtained from the IpaD protein fused to the lamprey VLR-B antibody C-terminal domain SEQ ID NO: 2 is of great interest, since increased stability should increase the shelf-life of an immunogenic composition containing such an antigen. Furthermore, a thermostable recombinant protein antigen is also expected to have a longer in vivo stability when injected into a patient.

EXAMPLE 5

Polymerization of a Recombinant *Shigella flexneri* MxiH Protein Expressed in *E. coli*

The nucleic acid sequence coding for the MxiH protein from *Shigella flexneri* Serotype 2a Strain 301 was optimized for codon usage in *E. coli* by Geneart. This sequence is referred to herein as SEQ ID NO: 21.

SEQ ID NO: 21 was fused to the nucleic acid sequence SEQ ID NO: 4 also codon optimized for *E. coli* by Geneart to generate SEQ ID NO: 22. The corresponding protein sequence is SEQ ID NO: 23. SEQ ID NO: 21 and SEQ ID NO: 22 were also fused to a sequence coding for a polyhistidine-tag (6× His) via a GGSLE linker, thus generating SEQ ID NO: 24 (MxiH-His, the GGSLE linker is between the MxiH sequence and the His-tag) and SEQ ID NO: 25 (MxiH-lamprey-His, the GGSLE linker is between the MxiH-lamprey sequence and the His-tag) respectively.

SEQ ID NO: 21, SEQ ID NO: 22, SEQ ID NO: 24 and SEQ ID NO: 25 were each separately inserted into the NcoI/XhoI restriction site of the pM1800 expression cassette. Induction of the expression of the protein of interest is carried out via addition of IPTG 5 μg of the plasm ids containing the MxiH sequence with or without the polymerization sequence and with or without the linker and His-tag sequence were suspended in 10 μl of water. 0.5 μl of each suspension was added to either *E. coli* BL21 DE3 C6000-03 or *E. coli* Shuffle (B) ref C3029H and the bacteria were heat shocked as explained in example 4.

The samples were then cultured on LB medium, induced with IPTG, centrifuged and the cell pellets stored at −20° C. as described in Example 4.

The pellets were resuspended in 63 μl of Tris EDTA (10 mM Tris, 1 mM EDTA, pH 8.0, Novagen)+1 μl of Ready lyse 20 KU/μl (Epicentre) diluted at 1/20+1 μl of Benzonase 25 U/μl (Novagen). The samples were then agitated for 10 minutes at 37° C. before centrifugation at 13,000 rpm for 10 minutes.

60 μl of the supernatant was mixed with 20 μl of NuPAGE® LDS Sample Buffer (4×) (Invitrogen), while the pellet was suspended in 60 μl of Tris EDTA and 20 μl of NuPAGE® LDS Sample Buffer (4×) (Invitrogen).

15 μl of each sample was loaded and run on an SDS-PAGE gel (NuPAGE® 4-12% Bis-Tris gel, Life Technologies, Carlsbad, USA). 15 μl of SeeBlue® Plus2 Pre-Stained Standard (Life Technlologies) was used as a molecular weight marker.

pM1800 containing no MxiH sequence, inserted in IPTG-induced *E. coli,* served as a negative control. Sample separation was performed at 200V in MES buffer for 30 minutes (Life Technologies).

Western Blots of the SDS-PAGE gels were made as described in Example 4.

The blots were probed using a mouse polyclonal antibody against MxiH, diluted at 1/1000 in PBS, followed by Rabbit anti mouse IRDye 800 antibody (Rockland) diluted at 1/5000 in PBS. Another Western Blot was probed using a mouse monoclonal antibody against His (Sigma) diluted at 1/1000 in PBS, followed by Rabbit anti mouse IRDye 800 antibody (Rockland) diluted at 1/5000 in PBS. The blots were analyzed with an ODYSSEY (Li-Cor BioSciences) imaging system.

The results of the Western blots are shown in FIGS. 10 and 11. The results in FIG. 10, showing the blot probed with a mouse polyclonal antibody against MxiH, are similar to the ones observed with rHA in examples 1 and 3, and with IpaD in example 4, above. Indeed, FIG. 10 shows that the MxiH protein fused to the lamprey VLR-B antibody C-terminal domain SEQ ID NO: 2 was produced as dimers, trimers, tetramers, pentamers and other higher polymerized forms (the fusion MxiH-lamprey monomer has an expected molecular weight of 13.86 kDa) in the BL21 and Shuffle *E. coli* strains (with the strongest expression in Shuffle). MxiH was found in the pellet (insoluble fraction: IS on FIGS. 10 and 11). The results in FIG. 11, displaying the blot probed with a mouse monoclonal antibody against His, show that the addition of a His-Tag has no detrimental effect on the polymerization of the MxiH protein by the lamprey VLR-B antibody C-terminal domain SEQ ID NO: 2. In FIGS. 10 and 11 MxiH is not visible. The inventors consider that MxiH without a lamprey sequence is produced in a quantity too small to be revealed by the antibodies on the blots.

The invention claimed is:

1. A molecule comprising a first amino acid sequence with at least 80% identity to SEQ ID NO: 1 and at least two different amino acid sequences that are heterologous to said first sequence, wherein said molecule does not comprise a leucine-rich repeat (LRR) module from a lamprey VLR-B antibody.

2. The molecule of claim 1, wherein said molecule does not comprise a sequence selected from the group of sequences defined by SEQ ID NO: 29.

3. The molecule of claim 1, wherein the only amino acid sequence in said molecule which is derived from a lamprey VLR-B antibody is the sequence having at least 80% identity to SEQ ID NO: 1.

4. The molecule of claim 1, comprising cysteine residues at the positions within the molecule corresponding to positions 2, 7, 13, 19, 21, 24 and 27 of SEQ ID NO:1.

5. The molecule of claim 1, comprising SEQ ID NO: 2.

6. The molecule of claim 1, wherein there is a linker between the first amino acid sequence and the at least two different heterologous amino acid sequences.

7. The molecule of claim 1, wherein the at least two different heterologous amino acid sequences encode at least two different antigens.

8. The molecule of claim 7, wherein the at least two different antigens are selected from the group consisting of influenza virus, HIV, cytomegalovirus, dengue virus, yellow fever virus, tick-borne encephalitis virus, hepatitis virus, Japanese encephalitis virus, human papillomavirus, coxsackievirus, herpes simplex virus, rubella virus, mumps virus, measles virus, rabies virus, polio virus, rotavirus, respiratory syncytial virus, Ebola virus, Chikungunya virus, *Mycobacterium tuberculosis, Staphylococcus aureus, Staphylococcus epidermidis, E. coli, Clostridium difficile, Bordetella pertussis, Clostridium tetani, Haemophilus influenzae* type b, *Chlamydia pneumoniae, Chlamydia trachomatis, Porphyromonas gingivalis, Pseudomonas aeruginosa, Mycobacterium diphtherias, Shigella, Neisseria meningitidis, Streptococcus pneumoniae* and *Plasmodium falciparum.*

9. The molecule of claim 8, wherein one or more of the at least two different antigens are from influenza virus and are selected from a haemaglutinin (HA), a matrix 2 protein (M2), and a HAM2 fusion protein.

10. The molecule of claim 1, wherein the at least two different heterologous amino acid sequences encode at least two different antibodies, antibody fragments, or scaffolds.

11. The molecule of claim 10, wherein the at least two different antibodies or antibody fragments are selected from monoclonal antibodies, single domain antibodies (dAb's), single-chain variable fragments (scFv's), Fabs, F(ab')2's and diabodies (Db's).

12. A recombinant nucleic acid comprising a first nucleic acid sequence with at least 80% identity to SEQ ID NO: 3 and at least two different nucleic acid sequences that are heterologous to said first sequence, wherein said recombinant nucleic acid does not encode a leucine-rich repeat (LRR) module from a lamprey VLR-B antibody.

13. The recombinant nucleic acid of claim 12, wherein said first nucleic acid sequence encodes an amino acid sequence which comprises cysteine residues at positions within said amino acid sequence that correspond to positions 2, 7, 13, 19, 21, 24 and 27 of SEQ ID NO:1.

14. The recombinant nucleic acid of claim 12, comprising SEQ ID NO: 4.

15. An expression cassette comprising a recombinant nucleic acid of claim 12, wherein the recombinant nucleic acid is operably linked to a promoter.

16. A host cell transformed with an expression cassette of claim 15.

17. A pharmaceutical composition comprising the molecule of claim 1, and a pharmaceutically acceptable carrier or diluent.

18. A method for treating a subject in need thereof comprising administering the pharmaceutical composition of claim 17 to the subject.

19. A method for inducing an immune response to an antigen in a subject comprising administering an effective amount of the molecule of claim 7 to the subject.

20. A method for multimerizing a recombinant multi-specific antibody comprising:

a. fusing a first nucleic acid sequence having at least 80% identity to SEQ ID NO: 3 to at least two heterologous nucleic acid sequences coding for at least two different antibody or antibody fragment amino acid sequences, wherein the recombinant multi-specific antibody does not comprise a leucine-rich repeat (LRR) module from a lamprey VLR-B antibody, and b. expressing the fusion protein encoded by said nucleic acid sequence, under conditions which lead to the multimerization of said recombinant multi-specific antibody.

* * * * *

UNITED STATES PATENT AND TRADEMARK OFFICE
CERTIFICATE OF CORRECTION

PATENT NO. : 10,577,398 B2
APPLICATION NO. : 16/143079
DATED : March 3, 2020
INVENTOR(S) : Régis Sodoyer and Isabelle Legastelois Page 1 of 1

It is certified that error appears in the above-identified patent and that said Letters Patent is hereby corrected as shown below:

On the Title Page

In the section titled "Applicant," please delete "Lyons" and insert --Lyon--.

In the section titled "Assignee," please delete "Lyons" and insert --Lyon--.

In the Specification

In the description:

Column 7, Line 44, delete "conserved in the first io amino acid sequence" and insert --conserved in the first amino acid sequence--.

Column 8, Lines 40-41, delete "SEQ ID NO:1 or io SEQ ID NO:2" and insert --SEQ ID NO:1 or SEQ ID NO:2--.

Column 10, Line 66, delete "ora gB-UL130" and insert --or a gB-UL130--.

Column 24, Line 20, delete "plasm ids" and insert --plasmids--.

In the Claims

Column 68, Line 63, delete "Mycobacterium diphtherias" and insert --Mycobacterium diphtheriae--.

Signed and Sealed this
Ninth Day of June, 2020

Andrei Iancu
*Director of the United States Patent and Trademark Office*